US009387203B2

(12) United States Patent
Hübsch et al.

(10) Patent No.: US 9,387,203 B2
(45) Date of Patent: Jul. 12, 2016

(54) SUBSTITUTED AMINOINDANE- AND AMINOTETRALINECARBOXYLIC ACIDS AND THE USE THEREOF

(71) Applicant: BAYER PHARMA AKTIENGESELLSCHAFT, Berlin (DE)

(72) Inventors: Walter Hübsch, Wuppertal (DE); Michael Hahn, Langenfeld (DE); Alexandros Vakalopoulos, Hilden (DE); Volkhart Min-Jian Li, Velbert (DE); Frank Wunder, Wuppertal (DE); Johannes-Peter Stasch, Solingen (DE); Karl-Heinz Schlemmer, Wuppertal (DE); Friederike Stoll, Düsseldorf (DE); Niels Lindner, Wuppertal (DE); Eva Maria Becker-Pelster, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/414,297

(22) PCT Filed: Jul. 16, 2013

(86) PCT No.: PCT/EP2013/065020
§ 371 (c)(1),
(2) Date: Jan. 12, 2015

(87) PCT Pub. No.: WO2014/012935
PCT Pub. Date: Jan. 23, 2014

(65) Prior Publication Data
US 2015/0174113 A1 Jun. 25, 2015

(30) Foreign Application Priority Data
Jul. 20, 2012 (EP) .................... 12177283

(51) Int. Cl.
A61K 31/445 (2006.01)
A61K 31/45 (2006.01)
A61K 45/06 (2006.01)
A61K 31/197 (2006.01)
A61K 31/277 (2006.01)
A61K 31/4015 (2006.01)
A61K 31/415 (2006.01)
A61K 31/421 (2006.01)
C07C 255/54 (2006.01)
C07D 231/12 (2006.01)
C07C 229/50 (2006.01)
C07D 263/22 (2006.01)
C07D 207/27 (2006.01)
C07D 211/76 (2006.01)
A61K 31/24 (2006.01)
A61K 9/00 (2006.01)
A61K 9/20 (2006.01)
C07C 227/18 (2006.01)
A61K 9/08 (2006.01)
A61K 9/10 (2006.01)

(52) U.S. Cl.
CPC ............... *A61K 31/45* (2013.01); *A61K 9/0019* (2013.01); *A61K 9/0095* (2013.01); *A61K 9/2018* (2013.01); *A61K 9/2059* (2013.01); *A61K 31/197* (2013.01); *A61K 31/24* (2013.01); *A61K 31/277* (2013.01); *A61K 31/4015* (2013.01); *A61K 31/415* (2013.01); *A61K 31/421* (2013.01); *A61K 45/06* (2013.01); *C07C 227/18* (2013.01); *C07C 229/50* (2013.01); *C07C 255/54* (2013.01); *C07D 207/27* (2013.01); *C07D 211/76* (2013.01); *C07D 231/12* (2013.01); *C07D 263/22* (2013.01); *A61K 9/08* (2013.01); *A61K 9/10* (2013.01); *C07C 2102/08* (2013.01); *C07C 2102/10* (2013.01)

(58) Field of Classification Search
None
See application file for complete search history.

(56) References Cited

U.S. PATENT DOCUMENTS

| 4,873,262 | A  | 10/1989 | Junge et al.   |
|-----------|----|---------|----------------|
| 4,880,802 | A  | 11/1989 | Schohe et al.  |
| 6,693,102 | B2 | 2/2004  | Stasch et al.  |
| 6,743,798 | B1 | 6/2004  | Straub et al.  |
| 6,833,364 | B1 | 12/2004 | Straub et al.  |
| 6,939,989 | B2 | 9/2005  | Harter et al.  |

(Continued)

FOREIGN PATENT DOCUMENTS

| CA | 2 809 911 A1 | 3/2012 |
|----|--------------|--------|
| EP | 0 064 964 B1 | 8/1984 |

(Continued)

OTHER PUBLICATIONS

Bitler et al., "The Preparation and Properties of Crystalline Firefly Luciferin", Archives of Biochemistry and Biophysics, 1957, 72:358-368, McCollum-Pratt Institute and Department of Biology, Johns Hopkins University.

Gerlach et al., "Synthesis of Benzoic and Tetralone Carboxylic Acid Esters from Phenols by Palladium Catalyzed Alkoxy/Aryloxy Carbonylation", Tetrahedron Letters, 1992, pp. 5499-5502, vol. 33, No. 38, Pergamon Press Ltd.

Hoenicka et al., "Purified soluble guanylyl cyclase expressed in a baculovirus/Sf9 system: stimulation by YC-1, nitric oxide, and carbon monoxide", J. Mol. Med., 1999, pp. 14-23, vol. 77, Springer-Verlag.

Takeuchi et al., "Rhodium Complex-Catalyzed Desilylative Cyclocarbonylation of 1-Aryl-2-(trimethylsilyl) acetylenes: A New Route to 2,3-Dihydro-1H-inden-1-ones", J. Org. Chem., 1993, pp. 5386-5392, vol. 58, American Chemical Society.

(Continued)

*Primary Examiner* — Heidi Reese
(74) *Attorney, Agent, or Firm* — Buchanan Ingersoll & Rooney PC

(57) ABSTRACT

The present application relates to novel substituted aminoindane- and aminotetralinecarboxylic acids, to processes for preparation thereof, to the use thereof for treatment and/or prevention of diseases, and to the use thereof for production of medicaments for treatment and/or prevention of diseases, especially for treatment and/or prevention of cardiovascular and cardiopulmonary diseases.

9 Claims, No Drawings

(56) References Cited

U.S. PATENT DOCUMENTS

| | | | |
|---|---|---|---|
| 7,067,694 | B2 | 6/2006 | Harter et al. |
| 7,087,644 | B1 | 8/2006 | Alonso-Alija et al. |
| 7,173,037 | B2 | 2/2007 | Alonso-Alija et al. |
| 7,700,653 | B2 | 4/2010 | Harter et al. |
| 8,420,656 | B2 | 4/2013 | Follmann et al. |
| 8,653,099 | B2 | 2/2014 | Colburn et al. |
| 8,673,903 | B2 | 3/2014 | Hübsch et al. |
| 8,921,377 | B2 | 12/2014 | Follmann et al. |
| 2002/0173514 | A1 | 11/2002 | Stasch et al. |
| 2004/0082658 | A1 | 4/2004 | Harter et al. |
| 2004/0082798 | A1 | 4/2004 | Alonso-Alija et al. |
| 2004/0092593 | A1 | 5/2004 | Harter et al. |
| 2004/0110840 | A1 | 6/2004 | Harter et al. |
| 2004/0176446 | A1 | 9/2004 | Alonso-Alija et al. |
| 2005/0288366 | A1 | 12/2005 | Harter et al. |
| 2006/0052397 | A1 | 3/2006 | Alonso-Alija et al. |
| 2006/0094769 | A1 | 5/2006 | Alonso-Alija et al. |
| 2006/0111444 | A1 | 5/2006 | Harter et al. |
| 2009/0203906 | A1 | 8/2009 | Alonso-Alija et al. |
| 2010/0317854 | A1 | 12/2010 | Alonso-Alija et al. |
| 2012/0022084 | A1 | 1/2012 | Follmann et al. |
| 2013/0203751 | A1 | 8/2013 | Hubsch et al. |
| 2013/0237551 | A1 | 9/2013 | Follmann et al. |
| 2013/0267548 | A1 | 10/2013 | Follmann et al. |
| 2014/0031391 | A1 | 1/2014 | Hahn et al. |
| 2014/0148433 | A1 | 5/2014 | Follmann et al. |
| 2014/0350020 | A1 | 11/2014 | Follmann et al. |

FOREIGN PATENT DOCUMENTS

| | | |
|---|---|---|
| EP | 0 041 488 A1 | 5/1993 |
| EP | 0 270 947 B1 | 5/1993 |
| FR | 2 659 853 A1 | 3/1990 |
| WO | 90/15047 A1 | 12/1990 |
| WO | WO 95/18617 A1 | 7/1995 |
| WO | 99/62505 A3 | 12/1999 |
| WO | WO 00/06568 A1 | 2/2000 |
| WO | WO 00/06569 A1 | 2/2000 |
| WO | WO 00/35882 A1 | 6/2000 |
| WO | WO 01/19780 A1 | 3/2001 |
| WO | WO 02/42301 A1 | 5/2002 |
| WO | WO 02/070459 A1 | 9/2002 |
| WO | WO 02/070460 A1 | 9/2002 |
| WO | WO 02/070461 A1 | 9/2002 |
| WO | WO 02/070462 A1 | 9/2002 |
| WO | WO 02/070510 A2 | 9/2002 |
| WO | WO 03/095451 A1 | 11/2003 |
| WO | 2005/012291 A1 | 2/2005 |
| WO | WO 2006/104826 A2 | 10/2006 |
| WO | 2009/023669 A1 | 2/2009 |
| WO | 2009/032249 A1 | 3/2009 |
| WO | WO 2011/141409 A1 | 11/2011 |
| WO | WO 2011/147809 A1 | 12/2011 |
| WO | WO 2012/004258 A9 | 1/2012 |
| WO | WO 2012/028647 A1 | 3/2012 |
| WO | WO 2012/059549 A1 | 5/2012 |
| WO | 2013/157528 A1 | 10/2013 |
| WO | WO 2013157528 A1 * | 10/2013 |

OTHER PUBLICATIONS

Witte et al., "Experimental heart failure in rats: effects on cardiovascular circadian rhythms and on myocardial β-adrenergic signaling" Cardiovascular Research, 2000, pp. 350-358, vol. 47, Elsevier.

Wunder et al., "A cell-based cGMP assay useful for ultra-high-throughput screening and identification of modulators of the nitric oxide/cGMP pathway", Analytical Biochemistry, 2005, pp. 104-112, vol. 339, Elsevier.

International Preliminary Report on Patentability and the Written Opinion of the International Searching Authority (Forms PCT/IB/338, PCT/IB/373 and PCT/ISA/237) issued on Jan. 29, 2015, by the International Bureau of WIPO, in corresponding International Application No. PCT/EP2013/065020. (8 pages).

Evgenov et al., "Inhaled Agonists of Soluble Guanylate Cyclase Induce Selective Pulmonary Vasodilation," Am. J. Respir. Crit. Care Med., 2007, 176:1138-1145 (8 pages).

Bice et al., "NO-independent stimulation or activation of soluble guanylyl cyclase during early reperfusion limits infarct size," Cardiovascular Research, Oxford Journal of Medicine, 2014, 101:220-228 (9 pages).

Blanco et al., "Hemodynamic and Gas Exchange Effects of Sildenafil in Patients with Chronic Obstructive Pulmonary Disease and Pulmonary Hypertension," Am. J. Respir. Crit. Care Med., 2010, 181:270-278 (9 pages).

Ghofrani et al., "Neue Therapieoptionen in der Behandlung der pulmonalarteriellen Hypertonie," Herz, 2005, 30(4):296-302 (7 pages), abstract only.

Ghosh et al., "Studies on Oxygen Heterocycles Part-1 : Acid Catalysed and Photochemical Reactions of Some Aryldiazoketones," Tetrahedron, 1989, 45(5):1441-1446 (6 pages).

Greene et al., "The Role of Protective Groups in Organic Synthesis," Fourth Edition, Wiley, New York, 2007, 1-15 (15 pages).

Hoeper et al., "Diagnosis, Assessment, and Treatment of Non-Pulmonary Arterial Hypertension Pulmonary Hypertension," Journal of the Am. College of Cardiology, 2009, 54(1):S85-S96 (12 pages).

Horig et al.: "From bench to clinic and back: Perspective on the 1st IOPC Translational Research conference," Journal of Translational Medicine, Dec. 2004, 2:44 (8 pages).

Humbert et al., "Cellular and Molecular Pathobiology of Pulmonary Arterial Hypertension," Journal of the Am. College of Cardiology, 2004, 43(12):S13-S24 (12 pages).

Humbert et al, "The 4th World Symposium on Pulmonary Hypertension," Journal of the Am. College of Cardiology, 2009, 54(1):S1-S2 (2 pages).

Ito et al., "Current Drug Targets and Future Therapy of Pulmonary Arterial Hypertension," Current Med. Chemistry, 2007, 14:719-733 (15 pages).

Liu et al., "(R )- and (S)-5,6,7,8-Tetrahydro-l-hydroxy-N,N-dipropyl-9H-benzocyclohepten-8-ylamine. Stereoselective Interactions with 5-HTIA Receptors in the Brain," J. Med. Chem., 1989, 32:2311-2318 (8 pages).

Martin et al., "Structure of Cinaciguat (BAY 58-2667) Bound to Nostoc H-NOX Domain Reveals Insights into Heme-mimetic Activation of the Soluble Guanylyl Cyclase," Journal of Biol. Chem., Jul. 16, 2010, 285(29):22651-22657 (8 pages).

Montani et al., "Updated clinical classification of pulmonary hypertension," Pulmonary Circulation: Diseases and Their Treatment (3rd ed., Hodder Arnold Pub., Peacock et al., Eds.), 2011, 197-206 (13 pages).

Nossaman et al., "Stimulators and Activators of Soluble Guanylate Cyclase: Review and Potential Therapeutic Indications," Critical Care Research and Practice, 2012, Article ID 290805: 1-12 (12 pages).

Pettit et al., "Synthesis of the 6- and 7-Hydroxy-5,8-dioxocarbostyrils," Journal of Organic Chemistry, Mar. 1968, 33(3):1089-1092 (4 pages).

Rosenzweig, "Emerging treatments for pulmonary arterial hypertension," Expert Opinion Emerging Drugs, 2006, 11(4):609-619 (11 pages).

Schafer et al.: "Failure is an option: learning from unsuccessful proof-of-concept trials," Drug Discovery Today, 2008, 13(21/22): 913-916 (4 pages).

Schmidt et al., "NO- and Haem-Independent Soluble Guanylate Cyclase Activators," Handbook of Experimental Pharmacology, 2009, 191:309-339 (31 pages).

Stachel et al., "Discovery of pyrrolidine-based b-secretase inhibitors: Lead advancement through conformational design for maintenance of ligand binding efficiency," Bioorganic & Med. Chem. Letters, 2012, 22:240-244 (5 pages).

Stolz et al., "A randomised, controlled trial of bosentan in severe COPD," European Respir. Journal, 32(3):619-628 (10 pages).

Vanejevs et al., "Positive and Negative Modulation of Group I Metabotropic Glutamate Receptors," Journal Med. Chem., 2008, 51:634-647 (14 pages).

(56) References Cited

OTHER PUBLICATIONS

International Search Report (PCT/ISA/210) mailed on Oct. 10, 2013, by the European Patent Office as the International Searching Authority for International Application No. PCT/EP2013/065020.

Oleg V. Evgenov et al., "NO-independent stimulators and activators soluble guanylate cyclase: discovery and therapeutic potential", *Nature Reviews Drug Discovery*, vol. 5, Sep. 2006, 755-768.

Johannes-Peter Stasch et al., "NO- and haem-independent activation of soluble guanylyl cyclase: molecular basis and cardiovascular implications of a new pharmacological principle", *The British Journal of Pharmacology*, vol. 136, Jan. 24, 2002, pp. 773-783.

Johannes-Peter Stasch et al., "Targeting the heme-oxidized nitric oxide receptor for selective vasodilatation of diseased blood vessels", *The Journal of Clinical Investigation*, vol. 116, No. 9, Sep. 2006, pp. 2552-2561.

Becker et al., ""Desaturation" Effects in a Model of Secondary Pulmonary Hypertension—Riociguat in Comparison," Pneumologie, 2011, 65 (Supplement 2):S122-S123 (in German) (2 pages).

* cited by examiner

SUBSTITUTED AMINOINDANE- AND AMINOTETRALINECARBOXYLIC ACIDS AND THE USE THEREOF

This application is the national stage entry under 35 USC 371 of PCT Application PCT/EP2013/065020, filed Jul. 16, 2013, which claims priority to EP Application No. 12177283.4 filed Jul. 20, 2012.

The present application relates to novel substituted aminoindane- and aminotetralinecarboxylic acids, to processes for preparation thereof, to the use thereof for treatment and/or prevention of diseases, and to the use thereof for production of medicaments for treatment and/or prevention of diseases, especially for treatment and/or prevention of cardiovascular and cardiopulmonary diseases.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory centre. This is of central importance for the activation mechanism. NO is able to bind to the iron atom of haem and thus markedly increase the activity of the enzyme. Haem-free preparations cannot, by contrast, be stimulated by NO. Carbon monoxide (CO) is also able to attack at the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which may lead, for example, to hypertension, platelet activation, increased cell proliferation, endothelial dysfunction, atherosclerosis, angina pectoris, heart failure, thromboses, stroke and myocardial infarct.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attacks at the central iron atom of haem. In addition to the side effects, the development of tolerance is one of the crucial disadvantages of this mode of treatment [O. V. Evgenov et al., Nature Rev. Drug Disc. 5 (2006), 755].

Substances which directly stimulate soluble guanylate cyclase, i.e. without previous release of NO, have been identified in recent years. The indazole derivative YC-1 was the first NO-independent but haem-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521. Together with the recently published structurally different substances CMF-1571 and A-350619, these compounds form the new class of the sGC stimulators [Evgenov et al., ibid.]. A common characteristic of this substance class is an NO—independent and selective activation of the haem-containing sGC. In addition, the sGC stimulators in combination with NO have a synergistic effect on sGC activation based on a stabilization of the nitrosyl-haem complex. The exact binding site of the sGC stimulators at the sGC is still being debated. If the haem group is removed from the soluble guanylate cyclase, the enzyme still has a detectable catalytic basal activity, i.e., as before, cGMP is formed. The remaining catalytic basal activity of the haem-free enzyme cannot be stimulated by any of the stimulators mentioned above [Evgenov et al., ibid.].

In addition, NO— and haem-independent sGC activators were identified, with BAY 58-2667 being a prototype of this class. Common characteristics of these substances are that, in combination with NO, they have only an additive effect on enzyme activation, and that the activation of the oxidized or haem-free enzyme is markedly stronger than that of the haem-containing enzyme [Evgenov et al., ibid.; J. P. Stasch et al., Br. J. Pharmacol. 136 (2002), 773; J. P. Stasch et al., J. Clin. Invest. 116 (2006), 2552]. It is evident from spectroscopic investigations that BAY 58-2667 displaces the oxidized haem group which, as a result of the weakened iron-histidine bond, is attached only weakly to the sGC. It has also been shown that the characteristic sGC haem-binding motif Tyr-x-Ser-x-Arg is imperative both for interaction of the negatively charged propionic acids of the haem group and for the activity of BAY 58-2667. Against this background, it is assumed that the binding site of BAY 58-2667 to sGC is identical to the binding site of the haem group [J. P. Stasch et al., J. Clin. Invest. 116 (2006), 2552].

The compounds described in the present invention are likewise capable of activating the haem-free form of soluble guanylate cyclase. This is also confirmed by the fact that firstly these novel activators display no synergistic effect with NO at the haem-containing enzyme and secondly their action cannot be blocked by the haem-dependent inhibitor of soluble guanylate cyclase, 1H-1,2,4-oxadiazolo[4,3-a]quinoxalin-1-one (ODQ), but is even potentiated by this inhibitor [cf. O. V. Evgenov et al., Nature Rev. Drug Disc. 5 (2006), 755; J. P. Stasch et al., J. Clin. Invest. 116 (2006), 2552].

Accordingly, it was an object of the present invention to provide novel compounds which act as activators of soluble guanylate cyclase in the manner described above and can be used as such in particular for the treatment and prevention of cardiovascular and cardiopulmonary disorders.

Various aminodicarboxylic acid derivatives for the treatment of cardiovascular disorders are known from the patent applications WO 01/19780-A2, WO 02/070459-A1, WO 02/070460-A1, WO 02/070461-A1, WO 02/070462-A1 and WO 02/070510-A2. WO 95/18617-A1 and WO 00/35882-A1 describe 1-aminoindane and 1-aminotetraline derivatives for the treatment of neurological disorders. WO 2006/104826-A2 discloses N-acylated 1-aminoindane-5-carboxamides and 1-aminotetraline-6-carboxamides as glucagon receptor antagonists for the treatment of diabetes.

The present invention provides compounds of the general formula (I)

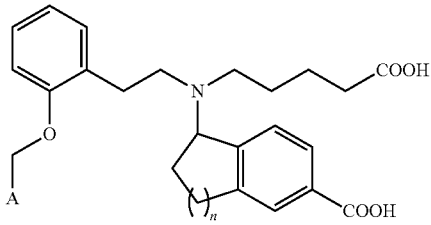

in which
n represents the number 1 or 2
and
A represents a group of the formula

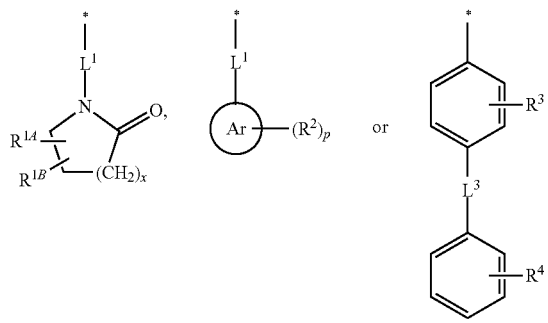

in which
* denotes the respective point of attachment to the remainder of the molecule,
$L^1$ represents straight-chain ($C_1$-$C_5$)-alkanediyl,
x represents the number 1, 2 or 3, where one of these $CH_2$ groups may be replaced by —O—,
$R^{1A}$ and $R^{1B}$ independently of one another represent hydrogen or methyl,
$L^2$ represents a bond or straight-chain ($C_1$-$C_5$)-alkanediyl,
Ar represents phenyl or 5- or 6-membered heteroaryl having up to three heteroatoms from the group consisting of N, O and S,
$R^2$ represents a substituent selected from the group consisting of fluorine, chlorine, bromine, cyano, ($C_1$-$C_4$)-alkyl, trifluoromethyl, ($C_1$-$C_4$)-alkoxy and trifluoromethoxy,
p represents the number 0, 1 or 2,
  where in the case where the substituent $R^2$ occurs twice, its respective meanings can be identical or different,
$L^3$ represents a bond, —O—, —$CH_2$—, —$CH_2$—$CH_2$— or —CH=CH—
and
$R^3$ and $R^4$ independently of one another represent hydrogen or a substituent selected from the group consisting of fluorine, chlorine, bromine, cyano, ($C_1$-$C_4$)-alkyl, trifluoromethyl, ($C_1$-$C_4$)-alkoxy and trifluoromethoxy,
and their salts, solvates and solvates of the salts.

Compounds according to the invention are the compounds of the formula (I) and their salts, solvates and solvates of the salts, the compounds encompassed by formula (I) of the formulae mentioned below and their salts, solvates and solvates of the salts and the compounds encompassed by formula (I) and mentioned below as working examples, and their salts, solvates and solvates of the salts, if the compounds encompassed by formula (I) and mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for the isolation, purification or storage of the compounds according to the invention.

Physiologically acceptable salts of the inventive compounds include acid addition salts of customary mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, N,N-ethyldiisopropylamine, monoethanolamine, diethanolamine, triethanolamine, dimethylaminoethanol, diethylaminoethanol, procaine, dicyclohexylamine, dibenzylamine, N-methylpiperidine, N-methylmorpholine, arginine, lysine and 1,2-ethylenediamine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example to an extension of the half-life in the body or to a reduction in the active dose required; such modifications of the compounds according to the invention may therefore in some cases also constitute a preferred embodiment of the present invention. Isotopic variants of the compounds according to the invention can be prepared by generally customary processes known to those skilled in the art, for example by the methods described below and the procedures reported in the working examples, by using corresponding isotopic modifications of the particular reagents and/or starting compounds therein.

In addition, the present invention also encompasses prodrugs of the compounds according to the invention. The term "prodrugs" refers here to compounds which may themselves be biologically active or inactive, but are converted while present in the body, for example by a metabolic or hydrolytic route, to compounds according to the invention.

The present invention comprises as prodrugs in particular hydrolysable ester derivatives of the carboxylic acids of the formula (I) according to the invention. These are to be understood as meaning esters which can be hydrolysed to the free carboxylic acids, as the main biologically active compounds, in physiological media, under the conditions of the biological tests described hereinbelow and in particular in vivo by enzymatic or chemical routes. $(C_1-C_4)$-alkyl esters, in which the alkyl group can be straight-chain or branched, are preferred as such esters. Particular preference is given to methyl, ethyl or tert-butyl esters.

In the context of the present invention, unless specified otherwise, the substituents are defined as follows:

In the context of the invention, $(C_1-C_4)$-alkyl represents a straight-chain or branched alkyl radical having 1 to 4 carbon atoms. Preferred examples include: methyl, ethyl, n-propyl, isopropyl, n-butyl, isobutyl, sec-butyl and tert-butyl.

$(C_1-C_5)$-alkanediyl, $(C_2-C_4)$-alkanediyl and $(C_2-C_4)$-alkanediyl in the context of the invention represent a straight-chain α,ω-divalent alkyl radical having 1 to 5, 1 to 4 and 2 to 4 carbon atoms, respectively. Preferred examples include: methylene, ethane-1,2-diyl(1,2-ethylene), propane-1,3-diyl (1,3-propylene), butane-1,4-diyl(1,4-butylene) and pentane-1,5-diyl(1,5-pentylene).

$(C_1-C_4)$-Alkoxy in the context of the invention represents a straight-chain or branched alkoxy radical having 1 to 4 carbon atoms. Preferred examples include: methoxy, ethoxy, n-propoxy, isopropoxy, n-butoxy, isobutoxy, sec-butoxy and tert-butoxy.

5- or 6-membered heteroaryl in the context of the invention represents an aromatic heterocycle (heteroaromatic) which has a total of 5 or 6 ring atoms, contains up to three identical or different ring heteroatoms from the group consisting of N, O and S and is attached via a ring carbon atom or optionally via a ring nitrogen atom. Preferred examples include: furyl, pyrrolyl, thienyl, pyrazolyl, imidazolyl, 1,2-oxazolyl (isoxazolyl), 1,3-oxazolyl, 1,2-thiazolyl (isothiazolyl), 1,3-thiazolyl, 1,2,3-Triazolyl, 1,2,4-triazolyl, 1,2,4-oxadiazolyl, 1,3,4-oxadiazolyl, 1,2,4-thiadiazolyl, 1,3,4-thiadiazolyl, pyridyl, pyrimidinyl, pyridazinyl, pyrazinyl, 1,2,4-triazinyl and 1,3,5-triazinyl.

In the context of the present invention, it is the case that for all radicals which occur more than once, their meaning is independent of the others. When radicals in the compounds according to the invention are substituted, the radicals may be mono- or polysubstituted, unless specified otherwise. Substitution by one or two identical or different substituents is preferred. Particular preference is given to substitution by one substituent.

A particular embodiment of the present invention comprises compounds of the formula (I) in which
n represents the number 2
and
A has the meanings given above,
and their salts, solvates and solvates of the salts.

A further particular embodiment of the present invention comprises compounds of the formula (I) in which
n represents the number 1 or 2
and
A represents a group of the formula

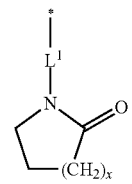

in which
* denotes the point of attachment to the remainder of the molecule,
$L^1$ represents straight-chain $(C_1-C_4)$-alkanediyl,
and
x represents the number 1 or 2, where one of these $CH_2$ groups may be replaced by —O—,
and their salts, solvates and solvates of the salts.

A further particular embodiment of the present invention comprises compounds of the formula (I) in which
n represents the number 1 or 2
and
A represents a group of the formula

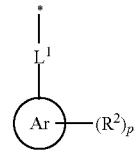

in which
* denotes the point of attachment to the remainder of the molecule,
$L^2$ represents a bond or straight-chain $(C_1-C_4)$-alkanediyl,
Ar represents phenyl,
$R^2$ represents a substituent selected from the group consisting of fluorine, chlorine, cyano, $(C_1-C_4)$-alkyl and trifluoromethyl
and
p represents the number 0, 1 or 2,
where in the case where the substituent $R^2$ occurs twice, its respective meanings can be identical or different,
and their salts, solvates and solvates of the salts.

A further particular embodiment of the present invention comprises compounds of the formula (I) in which
n represents the number 1 or 2
and
A represents a group of the formula

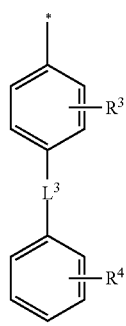

in which
* denotes the point of attachment to the remainder of the molecule,
$L^3$ represents a bond, —$CH_2$—$CH_2$— or —CH=CH—
and
$R^3$ and $R^4$ independently of one another represent hydrogen or a substituent selected from the group consisting of fluorine, chlorine, cyano, ($C_1$-$C_4$)-alkyl and trifluoromethyl, and their salts, solvates and solvates of the salts.

Preference is given in the context of the present invention to compounds of the formula (I) in which n represents the number 1 or 2
and
A represents a group of the formula

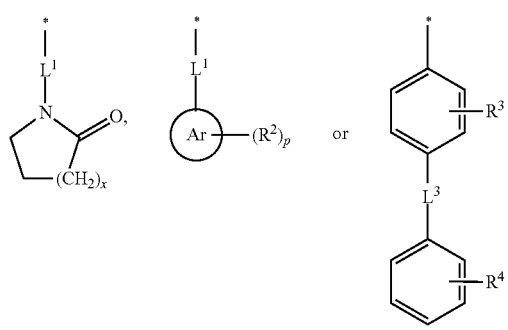

in which
* denotes the respective point of attachment to the remainder of the molecule,
$L^1$ represents straight-chain ($C_2$-$C_4$)-alkanediyl,
x represents the number 1 or 2, where one of these $CH_2$ groups may be replaced by —O—,
$L^2$ represents a bond or straight-chain ($C_1$-$C_4$)-alkanediyl,
Ar represents phenyl,
$R^2$ represents a substituent selected from the group consisting of fluorine, chlorine, cyano, ($C_1$-$C_4$)-alkyl and trifluoromethyl,
p represents the number 0 or 1,
$L^3$ represents a bond or —$CH_2$—$CH_2$—
and
$R^3$ and $R^4$ independently of one another represent hydrogen or a substituent selected from the group consisting of fluorine, chlorine, cyano, ($C_1$-$C_4$)-alkyl and trifluoromethyl, and their salts, solvates and solvates of the salts.

In the context of the present invention, particular preference is given to compounds of the formula (I) in which
n represents the number 1 or 2
and
A represents a group of the formula

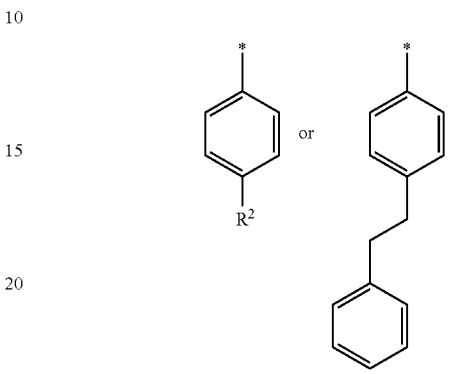

in which
* denotes the respective point of attachment to the remainder of the molecule and
$R^2$ represents methyl, ethyl, isopropyl or tert-butyl,
and their salts, solvates and solvates of the salts.

The individual radical definitions specified in the particular combinations or preferred combinations of radicals are, independently of the particular combinations of the radicals specified, also replaced as desired by radical definitions of other combinations.

Very particular preference is given to combinations of two or more of the abovementioned preferred ranges.

The invention furthermore provides a process for preparing the compounds of the formula (I) according to the invention, characterized in that a compound of the formula (II)

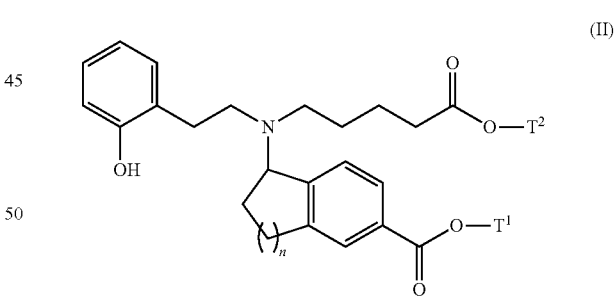

in which n has the meanings given above
and
$T^1$ and $T^2$ are identical or different and represent ($C_1$-$C_4$)-alkyl is reacted in the presence of a base with a compound of the formula (III)

in which A has the meanings given above
and $X^1$ represents a leaving group, for example chlorine, bromine, iodine, mesylate, triflate or tosylate, to give a compound of the formula (IV)

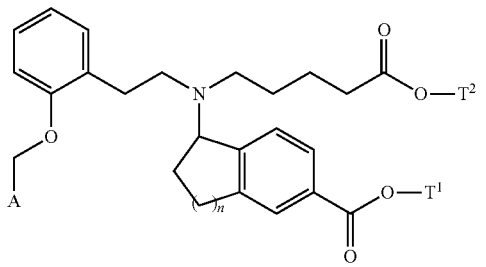

(IV)

in which n, A, $T^1$ and $T^2$ each have the meanings given above, and this is then converted by hydrolysis of the ester groupings —C(O)O$T^1$ and —C(O)O$T^2$ into the corresponding dicarboxylic acid of the formula (I)

and the resulting compounds of the formula (I) are optionally separated into the enantiomers and/or diastereomers thereof and/or optionally reacted with the appropriate (i) solvents and/or (ii) bases or acids to give the solvates, salts and/or solvates of the salts thereof.

Suitable inert solvents for the process step (II)+(III)→(IV) are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane, heptane, cyclohexane or mineral oil fractions, or dipolar aprotic solvents such as acetone, methyl ethyl ketone, acetonitrile, N,N-dimethylformamide (DMF), N,N-dimethylacetamide (DMA), dimethyl sulphoxide (DMSO), N,N'-dimethylpropyleneurea (DMPU) or N-methylpyrrolidinone (NMP). It is also possible to use mixtures of these solvents. Preference is given to using acetonitrile or dimethylformamide.

Suitable bases for the process step (II)+(III)→(IV) are in particular alkali metal carbonates such as sodium carbonate, potassium carbonate or caesium carbonate, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organometallic compounds such as n-butyllithium or phenyllithium. The base used is preferably sodium carbonate, potassium carbonate or caesium carbonate. If appropriate, the addition of an alkylation catalyst, for example lithium bromide, sodium iodide, potassium iodide, tetra-n-butylammonium bromide or benzyltriethylammonium chloride, is advantageous.

The reaction (II)+(III)→(IV) is generally carried out in a temperature range of from 0° C. to +150° C., preferably at from +20° C. to +100° C.

The hydrolysis of the ester groups —C(O)O$T^1$ and —C(O)O$T^2$ in process step (IV)→(I) is carried out using customary methods, by treating the esters in inert solvents with acids or bases, where in the latter variant the salts initially formed are converted to the free carboxylic acids by treating with acid. In the case of the tert-butyl esters, ester cleavage is preferably carried out using acids.

In the case of different groups $T^1$ and $T^2$, the hydrolysis can optionally be carried out simultaneously in a one-pot reaction or in two separate reaction steps.

Suitable inert solvents for these reactions are water or the organic solvents customary for ester cleavage. These preferably include alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetone, methyl ethyl ketone, N,N-dimethylformamide or dimethyl sulphoxide. It is equally possible to use mixtures of these solvents. In the case of a basic ester hydrolysis, preference is given to using mixtures of water with dioxane, tetrahydrofuran, methanol, ethanol, dimethylformamide and/or dimethyl sulphoxide. In the case of the reaction with trifluoroacetic acid, preference is given to using dichloromethane, and in the case of the reaction with hydrogen chloride preference is given to using tetrahydrofuran, diethyl ether, dioxane or water.

Suitable bases are the customary inorganic bases. These include in particular alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to lithium hydroxide, sodium hydroxide or potassium hydroxide.

Suitable acids for the ester cleavage are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is effected generally within a temperature range from −20° C. to +120° C., preferably at 0° C. to +80° C.

The process steps described above can be carried out at atmospheric, elevated or reduced pressure (for example in the range from 0.5 to 5 bar); in general, the reactions are each carried out at atmospheric pressure.

For their part, the compounds of the formula (II) can be prepared by reacting a keto compound of the formula (V)

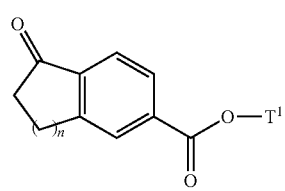

(V)

in which n and $T^1$ have the meanings given above in a reductive amination with 2-(2-methoxyphenyl)ethylamine (VI)

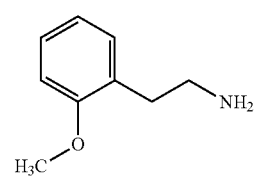

(VI)

to give a secondary amine of the formula (VII)

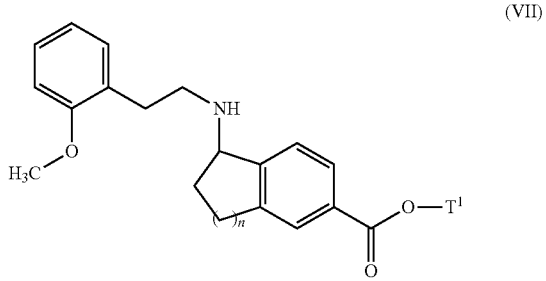

in which n and $T^1$ have the meanings given above, then alkylating in the presence of a base with a 5-halovaleric ester of the formula (VIII)

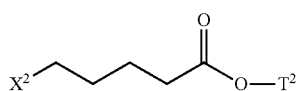

in which $T^2$ has the meaning given above
and
$X^2$ represents chlorine, bromine or iodine,
to give a tertiary amine of the formula (IX)

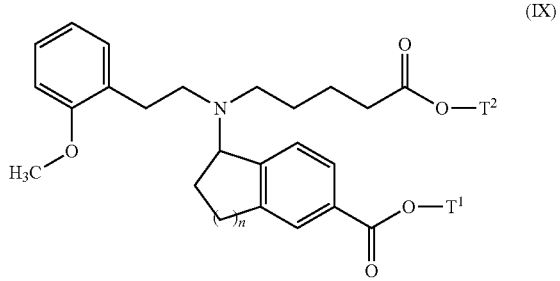

in which n, $T^1$ and $T^2$ each have the meanings given above
and then removing the phenolic methyl ether grouping by treatment with boron tribromide or hydrogen bromide.

The reaction (V)+(VI)→(VII) is carried out in a solvent which is customary for reductive aminations and inert under the reaction conditions, optionally in the presence of an acid and/or a dehydrating agent as catalyst. These solvents include, for example, tetrahydrofuran, toluene, dichloromethane, 1,2-dichloroethane, N,N-dimethylformamide and alcohols such as methanol, ethanol, n-propanol or isopropanol; it is also possible to use mixtures of such solvents. Preference is given to using methanol or ethanol. Suitable catalysts are customary organic acids such as acetic acid or p-toluenesulfonic acid.

Suitable reducing agents for these amination reactions are in particular borohydrides such as, for example, sodium borohydride, sodium cyanoborohydride, sodium triacetoxyborohydride or tetra-n-butylammonium borohydride; preference is given to using sodium borohydride.

The reaction (V)+(VI)→(VII) is generally carried out in a temperature range of from −20° C. to +50° C., preferably from 0° C. to +30° C.

The alkylation in process step (VII)+(VIII)→(IX) is carried out under analogous reaction conditions with regard to solvent, base and temperature, as described above for the reaction (II)+(III)→(IV). Here, the preferred bases and solvent used are alkali metal carbonates and acetonitrile, respectively. The alkylation is generally carried out in a temperature range from +50° C. to +100° C.

The cleavage of the phenolic methyl ether group in process step (IX)→(II) is carried out by customary methods by treatment with boron tribromide in dichloromethane at from −20° C. to +10° C. or by heating with a solution of hydrogen bromide in glacial acetic acid or water to from +100° C. to +130° C. If, under these reaction conditions, all or some of the ester groupings —C(O)O$T^1$ and —C(O)O$T^2$ are also simultaneously cleaved to give the corresponding free carboxylic acids of the formula (X)

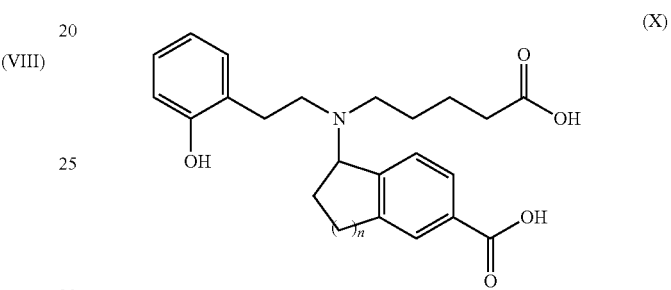

in which n has the meaning given above,
these can be re-esterified, for example, by subsequent treatment with methanol or ethanol in the presence of hydrogen chloride or thionyl chloride.

The reactions described above can be carried out at atmospheric, elevated or reduced pressure (for example in the range from 0.5 to 5 bar); in general, the reactions are each carried out at atmospheric pressure.

Separation of the compounds according to the invention into the corresponding enantiomers and/or diastereomers can, if expedient, also be carried out even at the stage of the compounds (II), (IV), (VII), (IX) or (X) which are then, in separated form, reacted further in accordance with the process sequences described above. Such a separation of stereoisomers can be carried out by customary methods known to the person skilled in the art. Preference is given to using chromatographic methods on achiral or chiral separation phases; in the case of carboxylic acids as intermediates or end products, separation may also alternatively be effected via diastereomeric salts using chiral bases.

The compounds of the formula (V) can be obtained using literature procedures [see, for example, for ethyl 1-oxoindane-5-carboxylate (n=1): R. Takeuchi and H. Yasue, *J. Org. Chem.* 1993, 58 (20), 5386-5392; for methyl 5-oxo-5,6,7,8-tetrahydronaphthalene-2-carboxylate (n=2): U. Gerlach and T. Wollmann, *Tetrahedron Lett.* 1992, 33 (38), 5499-5502].

The compounds of the formulae (III), (VI) and (VIII) are either commercially available or described as such in the literature, or they can be prepared in a way obvious to the person skilled in the art, in analogy to methods published in the literature. Numerous detailed procedures can also be found in the Experimental Part, in the section on the preparation of the starting compounds and intermediates.

The preparation of the compounds according to the invention can be illustrated by way of example by the following reaction scheme:

Scheme 1

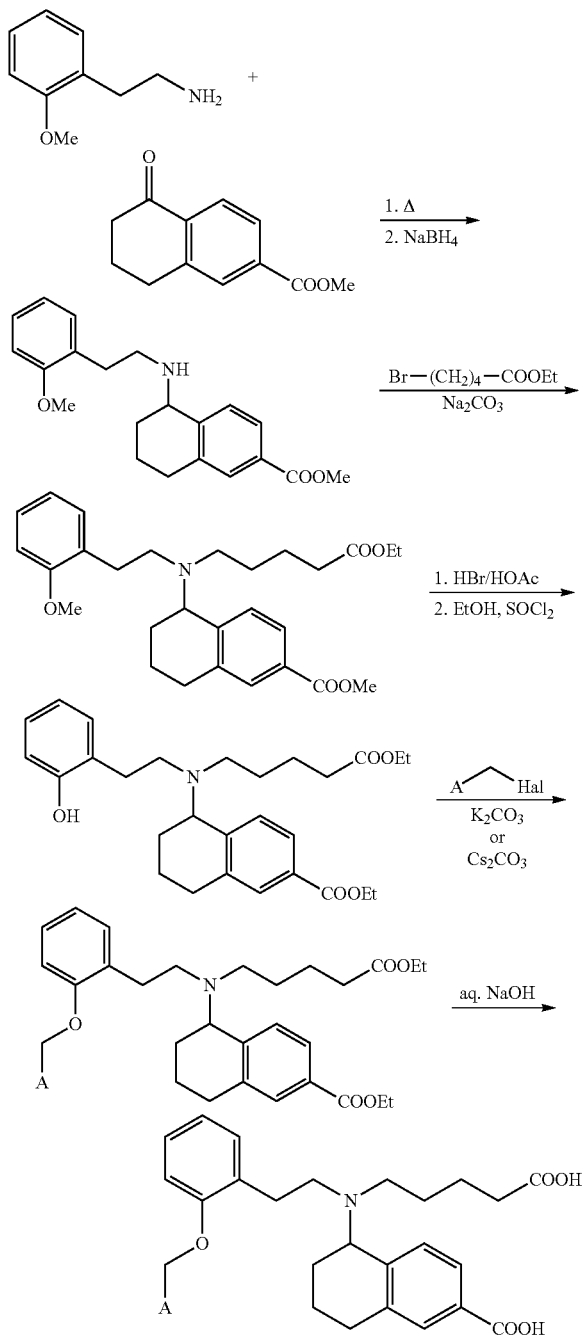

The compounds according to the invention have valuable pharmacological properties and can be used for prevention and treatment of diseases in humans and animals.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The compounds according to the invention are potent activators of soluble guanylate cyclase. They lead to vascular relaxation, inhibition of platelet aggregation and lowering of blood pressure, and they also increase coronary blood flow and microcirculation. These effects are mediated by a direct, haem-independent activation of soluble guanylate cyclase and an intracellular rise in cGMP.

The compounds according to the invention are especially suitable for treatment and/or prevention of cardiovascular, pulmonary, thromboembolic and fibrotic disorders.

Accordingly, the compounds according to the invention can be used in medicaments for the treatment and/or prevention of cardiovascular disorders such as, for example, high blood pressure (hypertension), heart failure, coronary heart disease, stable and unstable angina pectoris, pulmonary arterial hypertension (PAH) and other forms of pulmonary hypertension (PH), renal hypertension, peripheral and cardiac vascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV junctional extrasystoles, sick sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

In addition, the compounds according to the invention can also be used for treatment and/or prevention of arteriosclerosis, impaired lipid metabolism, hypolipoproteinaemias, dyslipidaemias, hypertriglyceridaemias, hyperlipidaemias, combined hyperlipidaemias, hypercholesterolaemias, abetalipoproteinaemia, sitosterolaemia, xanthomatosis, Tangier disease, adiposity, obesity and metabolic syndrome.

The compounds according to the invention can additionally be used for treatment and/or prevention of primary and secondary Raynaud's phenomenon, microcirculation impairments, claudication, tinnitus, peripheral and autonomic neuropathies, diabetic microangiopathies, diabetic retinopathy, diabetic ulcers on the extremities, gangrene, CREST syndrome, erythematosis, onychomycosis and rheumatic disorders.

In addition, the compounds according to the invention can be employed for the prevention of ischaemia- and/or reperfusion-related damage to organs or tissues and as additive for perfusion and preservation solutions for organs, organ parts, tissues or tissue parts of human or animal origin, in particular for surgical interventions or in the field of transplantation medicine.

The compounds according to the invention are also suitable for the treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also comprises the use of the compounds according to the invention for the treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds according to the invention are suitable for the treatment and/or prevention of disorders of the urogenital system such as, for example, benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence such as, for example, mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds according to the invention are also suitable for the treatment and/or prevention of asthmatic disorders, chronic-obstructive pulmonary diseases (COPD), acute respiratory distress syndrome (ARDS) and acute lung injury (ALI), alpha-1-antitrypsin deficiency (AATD), pulmonary fibrosis, pulmonary emphysema (for example cigarette smoke-induced pulmonary emphysema) and cystic fibrosis (CF) and also pulmonary arterial hypertension (PAH) and other forms of pulmonary hypertension (PH) including left-sided heart failure, HIV, sickle cell anaemia, thromboembolisms sarcoidosis, COPD or pulmonary fibrosis-associated pulmonary hypertension.

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prevention of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be employed for controlling states of pain.

In addition, the compounds according to the invention have anti-inflammatory action and can therefore be used as anti-inflammatory agents for treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, rheumatoid disorders, inflammatory skin disorders and inflammatory eye disorders.

Furthermore, the compounds according to the invention are suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring, naevi, diabetic retinopathy, proliferative vitroretinopathy and disorders of the connective tissue (for example sarcoidosis). The compounds according to the invention can also be used for promoting wound healing, for controlling postoperative scarring, for example as a result of glaucoma operations and cosmetically for ageing or keratinized skin.

By virtue of their property profile, the compounds according to the invention are particularly suitable for the treatment and/or prevention of cardiovascular disorders such as heart failure, angina pectoris, hypertension and pulmonary hypertension, and also of thromboembolic disorders and ischaemias, vascular disorders, impaired microcirculation, renal insufficiency, fibrotic disorders and arteriosclerosis.

The present invention further provides for the use of the inventive compounds for treatment and/or prevention of disorders, especially the aforementioned disorders.

The present invention further provides for the use of the compounds according to the invention for producing a medicament for the treatment and/or prevention of disorders, in particular the disorders mentioned above.

The present invention further provides a medicament comprising at least one of the compounds according to the invention, for the treatment and/or prevention of disorders, in particular the disorders mentioned above.

The present invention further provides for the use of the compounds according to the invention in a method for treatment and/or prevention of disorders, in particular the disorders mentioned above.

The present invention further provides a method for treatment and/or prevention of disorders, in particular the disorders mentioned above, using an effective amount of at least one of the compounds according to the invention.

The compounds according to the invention can be used alone or, if required, in combination with other active compounds. The present invention further provides medicaments comprising at least one of the inventive compounds and one or more further active ingredients, especially for treatment and/or prevention of the aforementioned disorders. Preferred examples of active compounds suitable for combinations include:

- organic nitrates and NO donors, for example sodium nitroprusside, nitroglycerin, isosorbide mononitrate, isosorbide dinitrate, molsidomine or SIN-1, and inhaled NO;
- compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 4 inhibitors such as roflumilast or revamilast and PDE 5 inhibitors such as sildenafil, vardenafil, tadalafil, udenafil, dasantafil, avanafil, mirodenafil or lodenafil;
- NO-independent but haem-dependent stimulators of guanylate cyclase, such as especially riociguat and the compounds described in WO 00/06568, WO 00/06569, WO 02/42301, WO 03/095451, WO 2011/147809, WO 2012/004258, WO 2012/028647 and WO 2012/059549;
- prostacyclin analogues and IP receptor agonists, by way of example and with preference iloprost, beraprost, treprostinil, epoprostenol or NS-304;
- edothelin receptor antagonists, by way of example and with preference bosentan, darusentan, ambrisentan or sitaxsentan;
- compounds which inhibit human neutrophile elastase (HNE), by way of example and with preference sivelestat or DX-890 (reltran);
- compounds which inhibit the signal transduction cascade, in particular from the group of the tyrosine kinase inhibitors, by way of example and with preference dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib, masitinib or tandutinib;
- Rho kinase-inhibiting compounds, by way of example and with preference fasudil, Y-27632, SLx-2119, BF-66851, BF-66852, BF-66853, KI-23095 or BA-1049;
- anti-obstructive agents as used, for example, for the therapy of chronic obstructive pulmonary disease (COPD) or bronchial asthma, such as, by way of example and with preference, inhalatively or systemically administered beta-receptor mimetics or inhalatively administered anti-muscarinergic substances;
- anti-inflammatory and/or immunosuppressive agents as used, for example, for the therapy of chronic obstructive pulmonary disease (COPD), bronchial asthma or pulmonary fibrosis, such as, by way of example and with preference, systemically or inhalatively administered corticosteroids;
- chemotherapeutics like those employed, for example, for the therapy of neoplasms in the lung or other organs.
- active compounds used for the systemic and/or inhalative treatment of pulmonary disorders, for example for cystic fibrosis (alpha-1-antitrypsin, aztreonam, ivacaftor, Lumacaftor, ataluren, amikacin, levofloxacin), chronic obstructive pulmonary disease (COPD) (LAS40464, PT003, SUN-101), acute respiratory distress syndrome (ARDS) and acute lung injury (ALI) (interferon-beta-1a, traumakines), obstructive sleep apnoea (VI-0521), bronchiectasis (mannitol, ciprofloxacin), bronchiolitis obliterans (cyclosporin, aztreonam) and sepsis (pagibaximab, Voluven, ART-123);
- antithrombotic agents, by way of example and with preference from the group of the platelet aggregation inhibitors, the anticoagulants or the profibrinolytic substances;
- hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or
- active compounds altering lipid metabolism, for example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, melagatran, dabigatran, bivalirudin or clexane.

In a preferred embodiment of the invention, the compounds according to the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embursatan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a diuretic, by way of example and with preference furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds according to the invention are administered in combination with a CETP inhibitor, by way of example and with preference torcetrapib (CP-529 414), HT-705 or CETP vaccine (Avant).

In a preferred embodiment of the invention, the compounds according to the invention are administered in combination with a thyroid receptor agonist, by way of example and with preference D-thyroxin, 3,5,3'-triiodothyronin (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, nontoxic, pharmaceutically suitable excipients, and the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

Suitable administration forms for oral administration are those which work according to the prior art and release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral, intrapulmonary (inhalative) and intravenous administration.

The compounds according to the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of from about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight. In the case of intrapulmonary administration, the amount is generally about 0.1 to 50 mg per inhalation.

It may nevertheless be necessary where appropriate to deviate from the stated amounts, specifically as a function of body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are in each case based on volume.

A. EXAMPLES

Abbreviations and Acronyms
abs. absolute
Ac acetyl
aq. aqueous, aqueous solution
ATP adenosine-5'-triphosphate
Brij® polyethylene glycol dodecyl ether
BSA bovine serum albumin
Ex. Example
c concentration
cat. catalytic
DMF N,N-dimethylformamide
DMSO dimethyl sulphoxide
DTT dithiothreitol
ee enantiomeric excess
ent enantiomerically pure, enantiomer
eq. equivalent(s)
ESI electrospray ionization (in MS)
Et ethyl
GTP guanosine-5'-triphosphate
h hour(s)
Hal halogen
HOAc acetic acid
HPLC high-pressure high-performance liquid chromatography
LC-MS liquid chromatography-coupled mass spectroscopy
Me methyl
min minute(s)
MS mass spectroscopy
NMR nuclear magnetic resonance spectroscopy
quant. quantitative (in yield)
rac racemic, racemate
RP reverse phase (in HPLC)
RT room temperature
$R_t$ retention time (in HPLC)
s.a. see above TEA triethanolamine
TFA trifluoroacetic acid
THF tetrahydrofuran
UV ultraviolet spectroscopy
v/v ratio by volume (of a solution)
tog. together HPLC and LC-MS Methods:

Method 1 (Preparative HPLC):
Column: Grom-Sil C18 10 μm, 250 mm×30 mm; mobile phase A: water+0.1% formic acid, mobile phase B: acetonitrile; program: 0-5 min 10% B, 5-38 min gradient to 95% B; flow rate: 50 ml/min; UV detection: 210 nm.

Method 2 (LC-MS):
Instrument: Waters Acquity SQD UPLC System; column: Waters Acquity UPLC HSS T3 1.8μ, 50 mm×1 mm; mobile phase A: 1 l of water+0.25 ml of 99% strength formic acid, mobile phase B: 1 l of acetonitrile+0.25 ml of 99% formic acid; gradient: 0.0 min 90% A→1.2 min 5% A→2.0 min 5% A; flow rate: 0.40 ml/min; oven: 50° C.; UV detection: 210-400 nm.

Method 3 (LC-MS):
MS instrument type: Waters Micromass Quattro Micro; HPLC instrument type: Agilent 1100 series; column: Thermo Hypersil GOLD 3μ, 20 mm×4 mm; mobile phase A: 1 l of water+0.5 ml of 50% strength formic acid, mobile phase B: 1 l of acetonitrile+0.5 ml of 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (LC-MS):
Instrument: Micromass Quattro Premier with Waters UPLC Acquity; column: Thermo Hypersil GOLD 1.9μ, 50 mm×1 mm; mobile phase A: 1 l of water+0.5 ml of 50% strength formic acid, mobile phase B: 1 l of acetonitrile+0.5 ml of 50% formic acid; gradient: 0.0 min 90% A→0.1 min 90% A→1.5 min 10% A→2.2 min 10% A; flow rate: 0.33 ml/min; oven: 50° C.; UV detection: 210 nm.

Method 5 (Chiral Analytical HPLC):
Stationary phase: Daicel OD-H; column: 250 mm×4 mm; UV detection: 230 nm; mobile phase: isopropanol/isohexane 30:70 (v/v); flow rate: 1.0 ml/min Method 6 (Chiral Analytical HPLC):
Stationary phase: Daicel OJ-H, 5 μm; column: 250 mm×4 mm; UV detection: 230 nm; mobile phase: isohexan/methanol/ethanol 50:25:25 (v/v/v); flow rate: 1.0 ml/min.

Method 7 (Chiral Analytical HPLC):
Stationary phase: Daicel Chiralpak IA; column: 250 mm×4 mm; UV detection: 230 nm; mobile phase: ethanol/methyl tert-butyl ether 75:25 (v/v); flow rate: 1.0 ml/min.

Method 8 (Preparative LC-MS):
MS instrument: Waters; HPLC instrument: Waters; column: Waters X-Bridge C18 5 μm, 18 mm×50 mm; mobile phase A: water+0.05% triethylamine, mobile phase B: acetonitrile+0.05% triethylamine; gradient: 0.0 min 95% A→0.15 min 95% A→8.0 min 5% A→9.0 min 5% A; flow rate: 40 ml/min; UV detection: DAD, 210-400 nm.

Method 9 (Preparative LC-MS):
MS instrument: Waters; HPLC instrument: Waters; column: Phenomenex Luna 5μ C18(2) 100A, 50 mm×21.2 mm; mobile phase A: water+0.05% formic acid, mobile phase B: acetonitrile+0.05% formic acid; gradient: 0.0 min 95% A→0.15 min 95% A→8.0 min 5% A→9.0 min 5% A; flow rate: 40 ml/min; UV detection: DAD, 210-400 nm.

Method 10 (LC-MS):
MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile+0.025% formic acid; gradient: 0.0 min 98% A→0.9 min 25% A→1.0 min 5% A→1.4 min 5% A→1.41 min 98% A→1.5 min 98% A; oven: 40° C.; flow rate: 0.60 ml/min; UV detection: DAD, 210 nm Starting Materials and Intermediates:

Example 1A rac-Methyl 5-{[2-(2-methoxyphenyl)ethyl]amino}-5,6,7,8-tetrahydronaphthalene-2-carboxylate

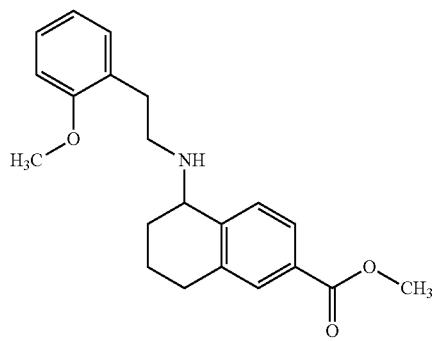 [SMILES: COC(=O)c1ccc2c(c1)CCCC2NCCc1ccccc1OC]

15.2 g (74.5 mmol) of methyl 5-oxo-5,6,7,8-tetrahydronaphthalene-2-carboxylate [U. Gerlach and T. Wollmann, *Tetrahedron Lett*. 1992, 33 (38), 5499-5502] and 11.5 g (74.5 mmol) of 2-(2-methoxyphenyl)ethylamine in 50 ml of ethanol were heated under reflux for 2 h. The mixture was then concentrated to dryness under reduced pressure, the residue was taken up in 300 ml of methanol and 5.6 g (149 mmol) of sodium borohydride were, over 20 min, added a little at a time at RT with slight external cooling to the suspension. The brownish solution was stirred at RT for 24 h and then poured into 900 ml of water and extracted three times with ethyl acetate. The combined organic phases were dried over sodium sulphate and concentrated. The residue (24.5 g) was purified by flash chromatography on silica gel using the mobile phase cyclohexane/ethyl acetate 2:1.

Yield: 21.0 g (83% of theory)

LC-MS (Method 4): $R_t$=0.87 min; MS (ESIpos): m/z=340 $[M+H]^+$ $^1$H-NMR (400 MHz, DMSO-$d_6$): δ [ppm]=7.56-7.79 (m, 2H), 7.47 (d, 1H), 7.04-7.28 (m, 2H), 6.94 (d, 1H), 6.86 (t, 1H), 3.82 (s, 3H), 3.73 (br. s, 1H), 2.61-2.91 (m, 6H), 1.59-1.95 (m, 5H).

Example 2A rac-Methyl 5-{(5-ethoxy-5-oxopentyl)[2-(2-methoxyphenyl)ethyl]amino}-5,6,7,8-tetrahydronaphthalene-2-carboxylate

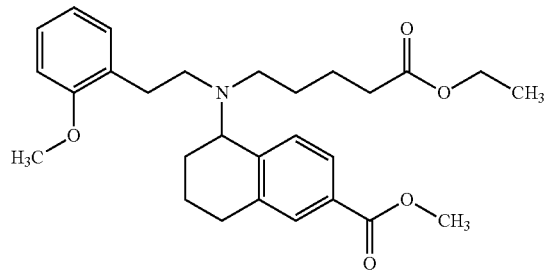 [SMILES: CCOC(=O)CCCCN(CCc1ccccc1OC)C1CCCc2cc(C(=O)OC)ccc21]

9.0 g (26.5 mmol) of the compound from Example 1A were dissolved in 100 ml of acetonitrile and 4.6 ml (6.1 g, 29.2 mmol) of ethyl 5-bromovalerate and 5.65 g (53 mmol) of sodium carbonate were added. The mixture was stirred under reflux for 3 days. After addition of a further 1.3 ml (8.2 mmol) of ethyl 5-bromovalerate and 1.6 g (15.1 mmol) of sodium carbonate, the mixture was stirred under reflux for another night. The same amounts of ethyl 5-bromovalerate and sodium carbonate were added again and the mixture was once more heated under reflux overnight until no more starting material could be detected by LC-MS. The mixture was then concentrated, water was added and the mixture was extracted repeatedly with ethyl acetate. The combined organic phases were dried over sodium sulphate and concentrated. The crude product (14.6 g) was purified by flash chromatography on silica gel using the mobile phase cyclohexane/ethyl acetate 5:1.

Yield: 11.6 g of an oil (87% of theory)

LC-MS (Method 2): $R_t$=0.93 min; MS (ESIpos): m/z=468 $[M+H]^+$ $^1$H-NMR (400 MHz, DMSO-$d_6$): δ [ppm]=7.55-7.70 (m, 3H), 6.95-7.21 (m, 2H), 6.74-6.93 (m, 2H), 3.90-4.14 (m, 4H), 3.82 (s, 3H), 3.64 (s, 3H), 3.54 (t, 1H), 2.57-2.82 (m, 4H), 2.33 (t, 1H), 2.13-2.26 (m, 2H), 1.87-2.07 (m, 2H), 1.74-1.87 (m, 1H), 1.34-1.71 (m, 8H), 1.06-1.21 (m, 4H) [further signals superimposed by DMSO peak].

Example 3A rac-Methyl 5-{[2-(2-hydroxyphenyl)ethyl](5-methoxy-5-oxopentyl)amino}-5,6,7,8-tetrahydronaphthalene-2-carboxylate

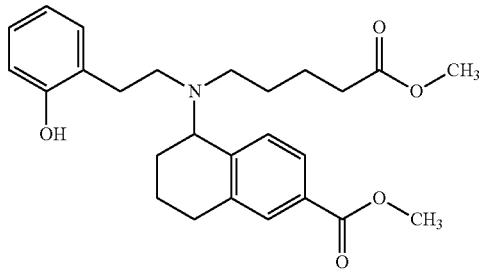 [SMILES: COC(=O)CCCCN(CCc1ccccc1O)C1CCCc2cc(C(=O)OC)ccc21]

Under argon, 653 mg (1.4 mmol) of the compound from Example 2A were dissolved in 12 ml of dichloromethane and the mixture was cooled to 0° C. 4.6 ml (4.6 mmol) of a 1 M solution of boron tribromide in dichloromethane were slowly added dropwise and the mixture was stirred at 0° C. for another 4 h (clear yellow solution). 7 ml of abs. methanol were then added and the mixture was heated under reflux overnight. The mixture was then concentrated to dryness under reduced pressure and the residue was partitioned between ethyl acetate and 10% strength aqueous sodium carbonate solution. The aqueous phase was re-extracted with ethyl acetate, and the combined organic phases were washed with saturated sodium chloride solution and dried over sodium sulphate. After concentration, the residue (519 mg of a brown oil) was purified by column chromatography on silica gel (mobile phase: gradient isohexane/4-32% ethyl acetate).

Yield: 172 mg of a yellow oil (20% of theory)

LC-MS (Method 3): $R_t$=1.62 min; MS (ESIpos): m/z=440 $[M+H]^+$.

Example 4A rac-Ethyl 5-{(5-ethoxy-5-oxopentyl)[2-(2-hydroxyphenyl)ethyl]amino}-5,6,7,8-tetrahydronaphthalene-2-carboxylate

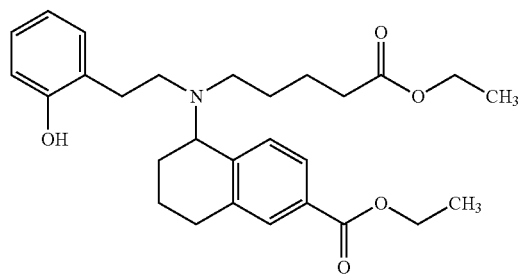 [SMILES: CCOC(=O)CCCCN(CCc1ccccc1O)C1CCCc2cc(C(=O)OCC)ccc21]

8.7 g (18.6 mmol) of the compound from Example 2A were stirred in 90 ml of a 33% strength solution of hydrogen bromide in glacial acetic acid under reflux overnight. After addition of another 90 ml of hydrogen bromide solution, the mixture was stirred at a bath temperature of 135° C. for a further night. The mixture was then concentrated under reduced pressure, another 40 ml of the solution of hydrogen bromide in glacial acetic acid were added to the residue and the mixture was stirred at a bath temperature of 110° C. for another night. The mixture was then once more concentrated to dryness. The residue, which comprised 77% of the dicarboxylic acid compound 5-{(4-carboxybutyl) [2-(2-hydroxyphenyl)ethyl]amino}-5,6,7,8-tetrahydronaphthalene-2-carboxylic acid [LC-MS (Method 2): $R_t$=0.64 min; MS (ESIpos): m/z=412 $[M+H]^+$], was subjected to incipient dissolution in 190 ml of ethanol, and 1.65 ml of thionyl chloride were added dropwise. The mixture was stirred at 70° C. overnight and then concentrated under reduced pressure. The residue (about 13 g) was taken up in ethyl acetate and washed twice with dilute aqueous sodium carbonate solution. The organic phase was dried over sodium sulphate and concentrated. The crude product (8.8 g) was purified by flash chromatography on silica gel using the mobile phase cyclohexane/ethyl acetate 5:1.

Yield: 5.3 g (56% of theory)

LC-MS (Method 2): $R_t$=0.86 min; MS (ESIpos): m/z=468 $[M+H]^+$ $^1$H-NMR (500 MHz, DMSO-$d_6$): δ [ppm]=9.21 (s, 1H), 7.54-7.76 (m, 3H), 6.93-7.04 (m, 2H), 6.61-6.78 (m, 2H), 4.29 (q, 2H), 4.21-4.36 (m, 2H), 3.92-4.11 (m, 4H), 2.66-2.81

(m, 3H), 2.35-2.66 (m, 6H), 2.13-2.27 (m, 2H), 1.89-2.08 (m, 3H), 1.36-1.69 (m, 6H), 1.31 (t, 3H), 1.11-1.22 (m, 4H).

Example 5A rac-Methyl 5-[(2-{2-[(4-tert-butylbenzyl)oxy]phenyl}ethyl)(5-methoxy-5-oxopentyl)amino]-5,6,7,8-tetrahydronaphthalene-2-carboxylate, formic acid salt

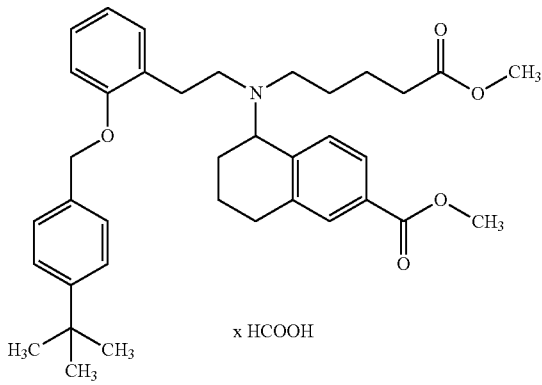 [SMILES: COC(=O)CCCCN(CCc1ccccc1OCc1ccc(C(C)(C)C)cc1)C1CCCc2cc(C(=O)OC)ccc21]

Under argon, 170 mg (0.387 mmol) of the compound from Example 3A, 104 mg (0.464 mmol) of 4-tert-butylbenzyl bromide and 403 mg (1.238 mmol) of caesium carbonate were stirred in 3 ml of DMF at RT for 2 h. 30 ml of water were then added, and the suspension was acidified with 5 N formic acid to pH 5. The mixture was extracted repeatedly with ethyl acetate, and the combined organic phases were dried over sodium sulphate and concentrated under reduced pressure. The residue (340 mg of a yellow oil) was purified by preparative HPLC (Method 1).

Yield: 133 mg (52% of theory)
LC-MS (Method 2): $R_t$=1.22 min; MS (ESIpos): m/z=586 [M+H]$^+$
$^1$H-NMR (400 MHz, DMSO-$d_6$): δ [ppm]=8.15 (s, 1H), 7.60 (m, 3H), 7.33 (d, 2H), 7.23 (d, 2H), 7.04-7.18 (m, 2H), 6.97 (d, 1H), 6.83 (t, 1H), 4.93 (dd, 2H), 3.89-3.97 (m, 1H), 3.81 (s, 3H), 3.55 (s, 3H), 2.73-2.83 (m, 1H), 2.63-2.73 (m, 2H), 2.34-2.45 (m, 2H), 2.14-2.21 (m, 2H), 1.82-1.98 (m, 2H), 1.32-1.59 (m, 6H), 1.27 (s, 9H) [further signals superimposed by the DMSO peak].

Example 6A and Example 7A

Methyl 5-[(2-{2-[4-tert-butylbenzyl)oxy]phenyl}ethyl)(5-methoxy-5-oxopentyl)amino]-5,6,7,8-tetrahydronaphthalene-2-carboxylate (enantiomers 1 and 2)

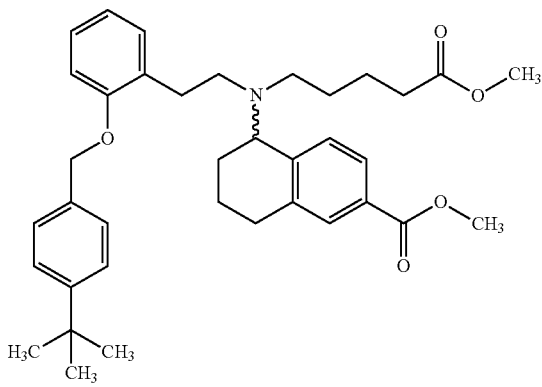 [SMILES: COC(=O)CCCCN(CCc1ccccc1OCc1ccc(C(C)(C)C)cc1)C1CCCc2cc(C(=O)OC)ccc21]

100 mg of the racemic methyl 5-[(2-{2-[(4-tert-butylbenzyl)oxy]phenyl}ethyl)(5-methoxy-5-oxopentyl)amino]-5,6,7,8-tetrahydronaphthalene-2-carboxylate from Example 5A were separated by preparative HPLC on a chiral phase into the enantiomers [sample preparation: the substance was dissolved in 3 ml of isopropanol and 7 ml of isohexane; injection volume: in each case 1 ml; column: Daicel Chiralpak OD-H, 250 mm×20 mm; eluent: isohexane/isopropanol 50:50 (v/v); flow rate: 15 ml/min, temperature: 30° C.; UV detection: 210 nm]:

Example 6A

Enantiomer 1

Yield: 25.5 mg
HPLC (Method 5): $R_t$=4.34 min, >99% ee
$^1$H-NMR (400 MHz, DMSO-$d_6$): δ [ppm]=7.60 (m, 3H), 7.33 (d, 2H), 7.24 (d, 2H), 7.04-7.18 (m, 2H), 6.97 (d, 1H), 6.83 (t, 1H), 4.92 (dd, 2H), 3.88-3.98 (m, 1H), 3.81 (s, 3H), 3.55 (s, 3H), 2.59-2.86 (m, 4H), 2.29-2.45 (m, 2H), 2.17 (t, 2H), 1.80-1.99 (m, 2H), 1.31-1.64 (m, 6H), 1.27 (s, 9H) [further signals superimposed by the DMSO peak].

Example 7A

Enantiomer 2

Yield: 22.6 mg
HPLC (Method 5): $R_t$=4.72 min, 90.5% ee

Example 8A rac-Ethyl 5-[(2-{2-[(4-tert-butylbenzyl)oxy]phenyl}ethyl)(5-ethoxy-5-oxopentyl)amino]-5,6,7,8-tetrahydronaphthalene-2-carboxylate

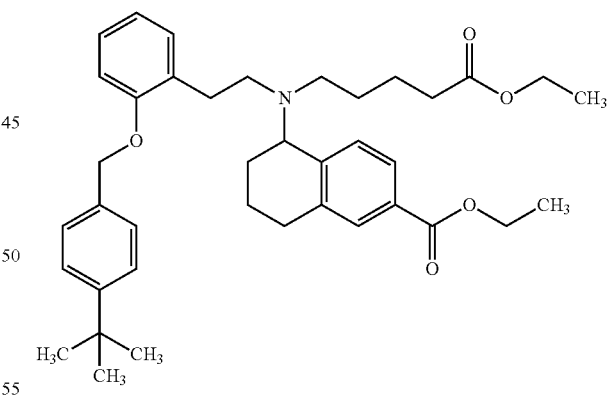

500 mg (1.07 mmol) of the compound from Example 4A were dissolved in 20 ml of DMF, 245 µl (1.23 mmol) of 4-tert-butylbenzyl bromide and 1.12 g (3.4 mmol) of caesium carbonate were added and the mixture was stirred at RT overnight. Water was then added to the mixture. After addition of 1.4 ml of 5 N formic acid, the mixture was extracted repeatedly with toluene and the combined organic phases were dried over sodium sulphate and concentrated.

Yield: 655 mg (purity 92%, 91% of theory)
LC-MS (Method 2): $R_t$=1.30 min; MS (ESIpos): m/z=614 [M+H]+.

Example 9A and Example 10A

Ethyl 5-[(2-[(4-tert-butylbenzyl)oxy]phenyl ethyl)(5-ethoxy-5-oxopentyl)amino]-5,6,7,8-tetrahydronaphthalene-2-carboxylate (enantiomers 1 and 2)

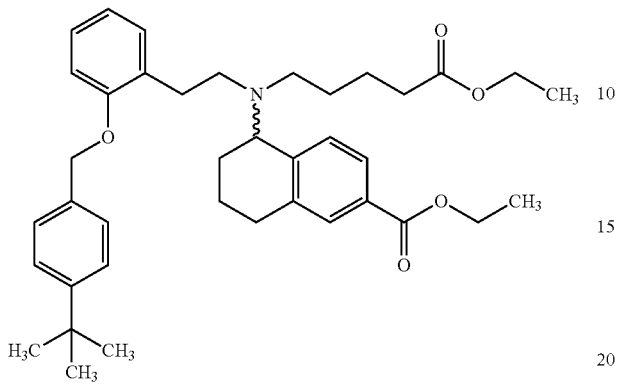

430 mg of the racemic ethyl 5-[(2-2-[(4-tert-butylbenzyl)oxy]phenyl ethyl)(5-ethoxy-5-oxopentyl)amino]-5,6,7,8-tetrahydronaphthalene-2-carboxylate from Example 8A were separated by preparative HPLC on a chiral phase into the enantiomers [sample preparation: the substance was dissolved in 20 ml of ethanol and 20 ml of isohexane; injection volume: in each case 0.5 ml; column: Daicel Chiralpak OJ-H, 5 μm, 250 mm×20 mm; mobile phase: isohexan/ethanol/methanol 95:2.5:2.5 (v/v/v); flow rate: 20 ml/min, temperature: 25° C.; UV detection: 230 nm]:

Example 9A

Enantiomer 1

Yield: 112 mg
HPLC (Method 6): $R_t$=5.65 min, >99.5% ee
LC-MS (Method 2): $R_t$=1.31 min; MS (ESIpos): m/z=614 [M+H]$^+$
$^1$H-NMR (500 MHz, DMSO-d$_6$): δ [ppm]=7.60 (s, 3H), 7.34 (d, 2H), 7.24 (d, 2H), 7.15 (t, 1H), 7.10 (d, 1H), 6.98 (d, 1H), 6.82 (t, 1H), 4.94 (dd, 2H), 4.22-4.31 (m, 2H), 3.97-4.05 (m, 2H), 3.89-3.97 (m, 1H), 2.73-2.82 (m, 1H), 2.52-2.73 (m, 5H), 2.33-2.45 (m, 2H), 2.16 (t, 2H), 1.82-1.98 (m, 2H), 1.32-1.59 (m, 6H), 1.23-1.31 (m, 13H), 1.14 (t, 3H).

Example 10A

Enantiomer 2

Yield: 79 mg
HPLC (Method 6): $R_t$=7,095 min, 82.7% ee
LC-MS (Method 2): $R_t$=1.32 min; MS (ESIpos): m/z=614 [M+H]$^+$.

Example 11A rac-Ethyl 1-{[2-(2-methoxyphenyl)ethyl]amino}indane-5-carboxylate

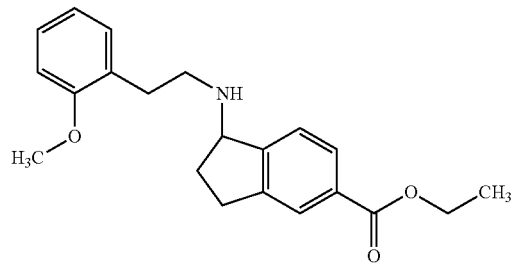 [SMILES: CCOC(=O)c1ccc2c(c1)CCC2NCCc1ccccc1OC]

The title compound was prepared analogously to the procedure for Example 1A starting with 2.0 g (9.73 mmol) of ethyl 1-oxoindan-5-carboxylate [R. Takeuchi and H. Yasue, *J. Org. Chem.* 1993, 58 (20), 5386-5392].

Yield: 2.46 g of a brownish oil (purity 87%)
LC-MS (Method 3): $R_t$=1.58 min; MS (ESIpos): m/z=340 [M+H]$^+$.

Example 12A rac-Ethyl 1-{(5-ethoxy-5-oxopentyl)[2-(2-methoxyphenyl)ethyl]amino}indane-5-carboxylate

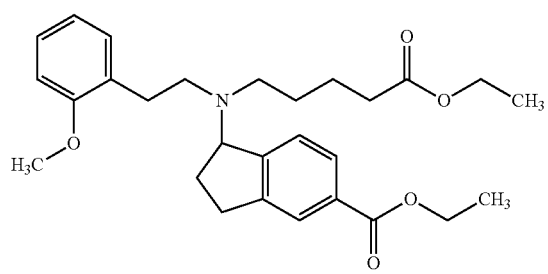 [SMILES: CCOC(=O)CCCCN(CCc1ccccc1OC)C1CCc2cc(C(=O)OCC)ccc21]

The title compound was prepared analogously to the procedure for Example 2A starting with 2.2 g (6.48 mmol) of the compound from Example 11A.

Yield: 1.87 g (62% of theory) of a yellowish oil
LC-MS (Method 2): $R_t$=0.93 min; MS (ESIpos): m/z=468 [M+H]$^+$
$^1$H-NMR (400 MHz, DMSO-d$_6$): δ [ppm]=7.69-7.79 (m, 2H), 7.11-7.19 (m, 2H), 7.07 (d, 1H), 6.89 (d, 1H), 6.82 (t, J=7.34 Hz, 1H), 4.53 (t, 1H), 4.29 (q, 2H), 4.03 (q, 2H), 3.66 (s, 3H), 2.56-2.95 (m, 4H), 2.35-2.48 (m, 2H), 2.18-2.26 (m, 2H), 2.08-2.18 (m, 1H), 1.82-1.95 (m, 1H), 1.37-1.61 (m, 4H), 1.31 (t, 3H), 1.16 (t, 3H).

Example 13A rac-1-{(4-Carboxybutyl)[2-(2-hydroxyphenyl)ethyl]amino}indane-5-carboxylic acid

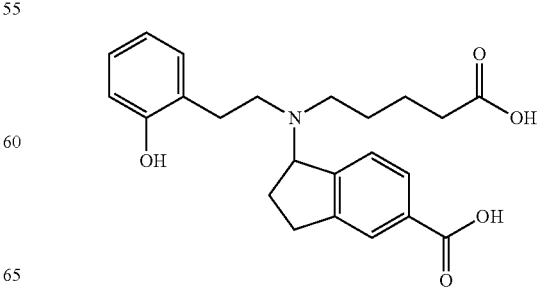

Analogously to the procedure for Example 3A, 1.8 g (3.85 mmol) of the compound from Example 12A gave 1.65 g of the crude phenol diester rac-ethyl 1-{(5-ethoxy-5-oxopentyl)[2-(2-hydroxyphenyl)ethyl]amino}indan-5-carboxylate [content 19%; LC-MS (Method 2): $R_t$=0.88 min; MS (ESIpos): m/z=454 [M+H]$^+$]. This crude product was heated under reflux in 10 ml of THF, 15 ml of methanol and 0.8 ml of 5 N aqueous sodium hydroxide solution for 2 h. The mixture was then concentrated to a volume of about 5 ml and acidified to pH 5-6 using 5 N formic acid. This resulted in the precipitation of an amorphous precipitate which was purified by silica gel chromatography (mobile phase dichloromethane/4-34% methanol) and subsequent preparative HPLC (Method 1).

Yield: 64 g (4% of theory) of a colourless solid.

LC-MS (Method 2): $R_t$=0.66 min; MS (ESIpos): m/z=398 [M+H]$^+$.

Example 14A rac-Ethyl 1-{(5-ethoxy-5-oxopentyl)[2-(2-hydroxyphenyl)ethyl]amino}indane-5-carboxylate hydrochloride

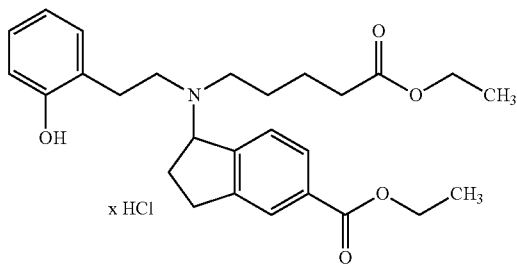 [SMILES: CCOC(=O)CCCCN(CCc1ccccc1O)C1CCc2cc(C(=O)OCC)ccc21]

53 mg (0.133 mmol) of the compound from Example 13A were dissolved in 3 ml of ethanol, 19 µl (0.27 mmol) of thionyl chloride were added and the mixture was stirred at 75° C. for 4 h. Another 200 µl of thionyl chloride were then added and stirring of the mixture was continued at 75° C. overnight. The mixture was then concentrated to dryness and the residue was co-evaporated twice with ethanol.

Yield: 60 mg (88% of theory) of a colourless amorphous solid.

LC-MS (Method 2): $R_t$=0.88 min; MS (ESIpos): m/z=454 [M+H]$^+$ $^1$H-NMR (400 MHz, DMSO-d$_6$): δ [ppm]=10.21-10.67 (broad, 1H), 7.83-8.06 (m, 3H), 6.96-7.20 (m, 2H), 6.65-6.90 (m, 2H), 5.20-5.42 (m, 1H), 4.33 (q, 2H), 3.96-4.13 (m, 2H), 2.85-3.21 (m, 7H), 2.68-2.81 (m, 1H), 2.34-2.44 (m, 2H), 2.23 (t, 1H), 1.38-1.97 (m, 4H), 1.33 (t, 3H), 1.07-1.22 (m, 3H) [further signals superimposed by water and DMSO peaks].

The following compounds were prepared analogously to the procedure for Example 5A:

| Example | Reactants | Structure | Yield; analytical data |
|---|---|---|---|
| 15A | Ex. 14A/ 4-tert-butylbenzyl bromide | (racemate) | 66% of theory; LC-MS (Method 2): $R_t$ = 1.20 min, m/z = 600 [M + H]$^+$; $^1$H-NMR(400 MHz, DMSO-d$_6$): δ [ppm] = 7.67-7.77 (m, 2H), 7.31-7.38 (m, 2H), 7.23-7.30 (m, 2H), 7.07-7.21 (m, 3H), 6.95-7.02 (m, 1H), 6.79-6.88 (m, 1H), 4.90-5.02 (m, 2H), 4.44-4.53 (m, 1H), 4.22-4.33 (m, 2H), 3.95-4.07 (m, 2H), 2.59-2.90 (m, 4H), 2.31-2.44 (m, 2H), 2.12-2.21 (m, 2H), 2.00-2.11 (m, 1H), 1.77-1.89 (m, 1H), 1.34-1.55 (m, 4H), 1.20-1.34 (m, 14H), 1.15 (s, 3H). |

| Example | Reactants | Structure | Yield; analytical data |
|---|---|---|---|
| 16A | Ex. 4A/ (3-chloropropyl) pyrrolidin-2-one | 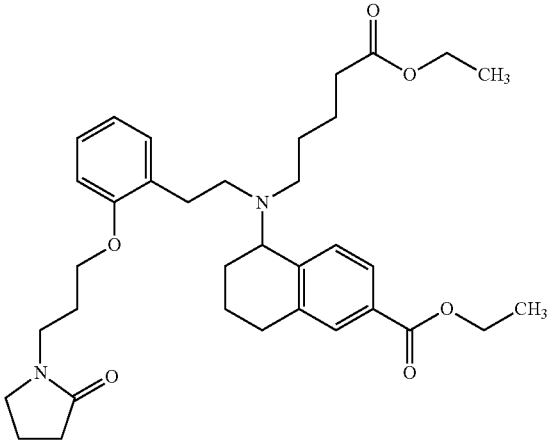<br>(racemate) | 66% of theory; LC-MS (Method 2): $R_t$ = 0.98 min, m/z = 593 [M + H]$^+$. |
| 17A | Ex. 16A$^{1)}$ | 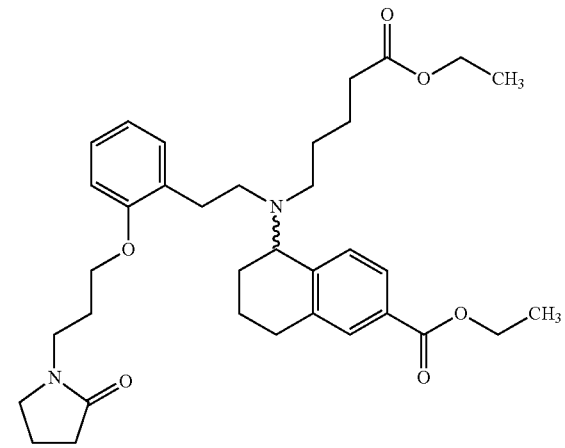<br>(enantiomer 1) | 45% of theory; LC-MS (Method 2): $R_t$ = 1.01 min, m/z = 593 [M + H]$^+$; HPLC (Method 6): $R_t$ = 4.89 min, 99.5% ee |
| 18A | Ex. 16A$^{1)}$ | 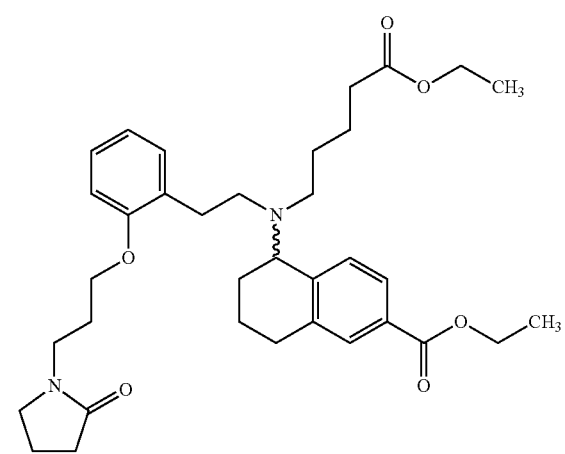<br>(enantiomer 2) | 59% of theory; LC-MS (Method 2): $R_t$ = 1.01 min, m/z = 593 [M + H]$^+$; HPLC (Method 6): $R_t$ = 7.16 min, 99.5% ee |

| Example | Reactants | Structure | Yield; analytical data |
|---|---|---|---|
| 19A | Ex. 4A/ 1-(chloromethyl)-4-(2-phenylethyl) benzene | (racemate) | 72% of theory; LC-MS (Method 2): $R_t$ = 1.34 min, m/z = 662 [M + H]$^+$; $^1$H-NMR (400 MHz, DMSO-$d_6$): δ [ppm] = 7.55-7.64 (m, 3H), 7.05-7.31 (m, 12H), 6.97 (d, 1H), 6.83 (t, 1H), 4.85-4.99 (m, 2H), 4.26 (q, 2H), 4.01 (q, 2H), 3.92 (br. s, 1H), 2.86 (s, 4H), 2.54-2.82 (m, 6H), 2.31-2.40 (m, 2H), 2.11-2.20 (m, 2H), 1.83-1.99 (m, 2H), 1.32-1.61 (m, 6H), 1.28 (t, 3H), 1.14 (t, 3H) [signals partially superimposed by DMSO peak]. |
| 20A | Ex. 4A/ 3-(3-chloropropyl)-1,3-oxazolidin-2-one | (racemate) | 76% of theory; LC-MS (Method 2): $R_t$ = 0.97 min, m/z = 595 [M + H]$^+$; $^1$H-NMR (400 MHz, DMSO-$d_6$): δ [ppm] = 7.56-7.66 (m, 3H), 7.04-7.18 (m, 2H), 6.78-6.89 (m, 2H), 4.19-4.34 (m, 4H), 3.93-4.07 (m, 3H), 3.78-3.93 (m, 2H), 3.48 (t, 2H), 3.22 (t, 2H), 2.55-2.82 (m, 5H), 2.16-2.26 (m, 2H), 1.86-2.07 (m, 2H), 1.80 (quin, 2H), 1.36-1.68 (m, 6H), 1.31 (t, 3H), 1.15 (t, 3H) [signals partially superimposed by DMSO peak]. |

[1]) Method for the Separation of Enantiomers:

Sample preparation: 71 mg of the racemate were dissolved in 8 ml of isopropanol and 10 ml of isohexane were added to the solution; injection volume: in each case 0.8 ml; column: Daicel Chiralpak OJ-H, 5 μm, 250 mm×20 mm; mobile phase: isohexan/ethanol/methanol 50:25:25 (v/v/v); flow rate: 20 ml/min, temperature: 25° C.; UV detection: 230 nm.

Working Examples

Example 1 rac-5-[(2-{2[(4-tert-Butylbenzyl)oxy]phenyl}ethyl)(4-carboxybutyl)amino]-5,6,7,8-tetrahydronaphthalene-2-carboxylic acid

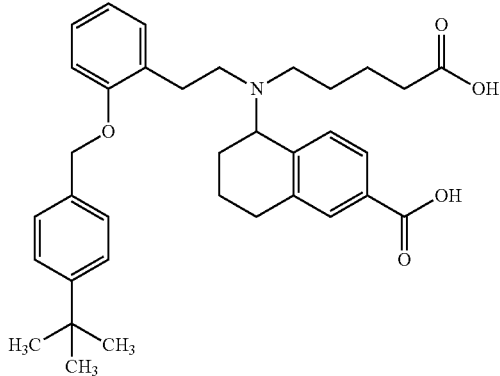

200 mg of the compound from Example 8A (purity 92%, 0.3 mmol) were dissolved in 4 ml of THF and 2 ml of methanol and, after addition of 345 μl (1.73 mmol) of 5 N aqueous sodium hydroxide solution, stirred under reflux for 1.5 h. The mixture was then diluted with water and the solvent was subsequently removed under reduced pressure. 650 μl of 5 N acetic acid were added, the mixture was cooled a little and the precipitated colourless solid was filtered off with suction and dried under high vacuum overnight.

Yield: 172 mg (quant.)

LC-MS (Method 2): $R_t$=1.03 min; MS (ESIpos): m/z=558 [M+H]$^+$ $^1$H-NMR (400 MHz, DMSO-d$_6$): δ [ppm]=7.53-7.64 (m, 3H), 7.35 (d, 2H), 7.24 (d, 2H), 7.15 (t, 1H), 7.09 (d, 1H), 6.98 (d, 1H), 6.83 (t, 1H), 4.93 (dd, 2H), 3.87-3.97 (m, 1H), 2.73-2.84 (m, 1H), 2.55-2.72 (m, 4H), 2.35-2.45 (m, 2H), 2.08-2.13 (m, 2H), 1.81-1.99 (m, 2H), 1.33-1.59 (m, 6H), 1.27 (s, 9H) [signals partially superimposed by DMSO peak].

Example 2

5-[(2-{2-[(4-tert-Butylbenzyl)oxy]phenyl}ethyl)(4-carboxybutyl)amino]-5,6,7,8-tetrahydronaphthalene-2-carboxylic acid (enantiomer 1)

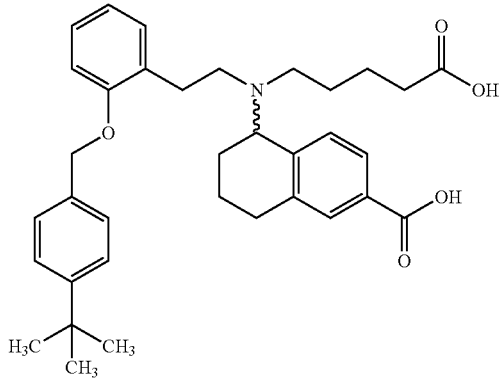 [SMILES: CC(C)(C)c1ccc(COc2ccccc2CCN(CCCCC(=O)O)C2CCCc3cc(C(=O)O)ccc32)cc1]

23 mg (0.039 mmol) of the compound from Example 6A were dissolved in 1 ml THF/water (5:1) and stirred with 0.4 ml of 1 N aqueous sodium hydroxide solution at RT overnight. 0.2 ml of methanol was then added and the mixture was stirred at RT for a further 2 h. 0.08 ml of 5 N formic acid was then added and the mixture was evaporated to dryness. The residue was purified by preparative HPLC (Method 1).

Yield: 14 g (62% of theory) of a colourless solid

LC-MS (Method 2): $R_t$=1.02 min; MS (ESIpos): m/z=558 [M+H]$^+$ $^1$H-NMR (400 MHz, DMSO-d$_6$): δ [ppm]=7.55-7.62 (m, 3H), 7.34 (d, 2H), 7.24 (d, 2H), 7.15 (t, 1H), 7.08 (d, 1H), 6.98 (d, 1H), 6.83 (t, 1H), 4.93 (dd, 2H), 3.88-3.97 (m, 1H), 2.73-2.83 (m, 1H), 2.58-2.73 (m, 4H), 2.39-2.46 (m, 2H), 2.09-2.15 (m, 2H), 1.82-1.99 (m, 2H), 1.32-1.58 (m, 6H), 1.27 (s, 9H) [signals partially superimposed by DMSO peak].

Example 3

5-[(2-{2-[(4-tert-Butylbenzyl)oxy]phenyl}ethyl)(4-carboxybutyl)amino]-5,6,7,8-tetrahydronaphthalene-2-carboxylic acid (enantiomer 2)

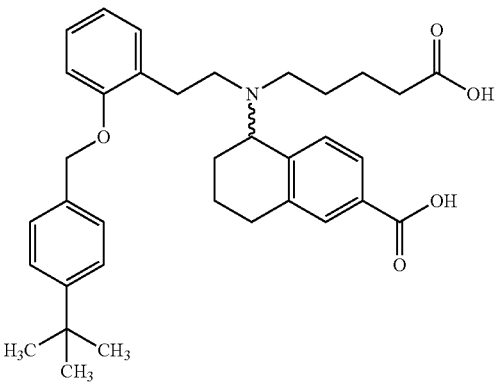

The title compound was obtained analogously to the procedure for Example 2 from 21 mg (0.036 mmol) of the compound from Example 7A.

Yield: 15.8 mg (79% of theory) of a colourless solid

LC-MS (Method 2): $R_t$=1.02 min; MS (ESIpos): m/z=558 [M+H]$^+$.

The following compounds were prepared analogously to the procedures for Examples 1 and 2.

| Example | Structure | Starting material | Yield; analytical data |
|---|---|---|---|
| 4 | (racemate) × HCOOH | 15A[1)4)] | 89% of theory; LC-MS (Method 2): $R_t = 0.97$ min, m/z = 544 [M + H]+ |
| 5 | (racemate) | 16A[2)4)] | 93% of theory; LC-MS (Method 2): $R_t = 0.75$ min, m/z = 537 [M + H]+ |
| 6 | (enantiomer 1) | 17A[3)4)] | 20% of theory; LC-MS (Method 2): $R_t = 1.73$ min, m/z = 537 [M + H]+ |

| Example | Structure | Starting material | Yield; analytical data |
|---|---|---|---|
| 7 | 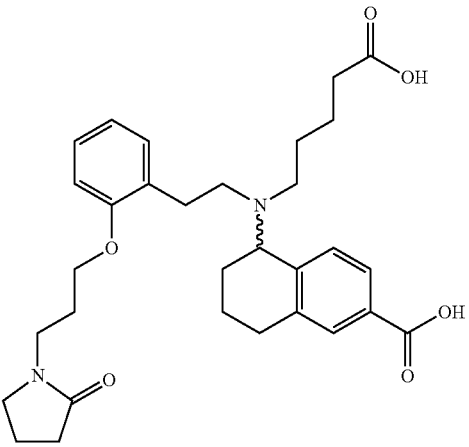<br>(enantiomer 2) | 18A[3)4)] | 26% of theory;<br>LC-MS (Method 2):<br>$R_t$ = 0.73 min,<br>m/z = 537 [M + H]$^+$ |
| 8 | 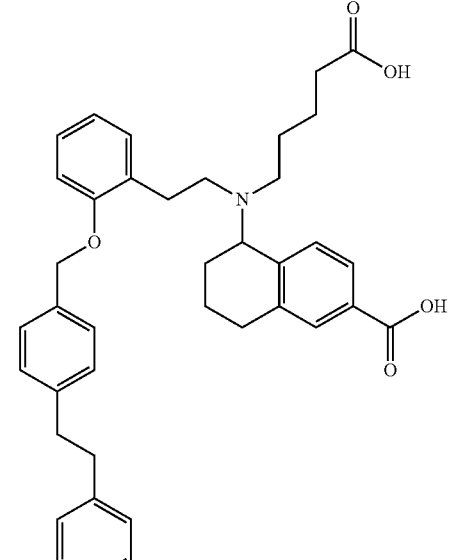<br>(racemate) | 19A[1)4)] | 62% of theory;<br>LC-MS (Method 2):<br>$R_t$ = 1.05 min,<br>m/z = 606 [M + H]$^+$<br>$^1$H-NMR (400 MHz, DMSO-$d_6$): δ [ppm] = 7.51-7.64 (m, 3H), 7.05-7.32 (m, 11H), 6.97 (d, 1H), 6.83 (t, 1H), 4.92 (dd, 2H), 3.91 (br. s, 1H), 2.82-2.92 (m, 4H), 2.55-2.82 (m, 6H), 2.43 (broad, 2H), 2.06-2.23 (m, 2H), 1.82-2.00 (m, 2H), 1.31-1.62 (m, 6H). |

| Example | Structure | Starting material | Yield; analytical data |
|---------|-----------|-------------------|------------------------|
| 9 | 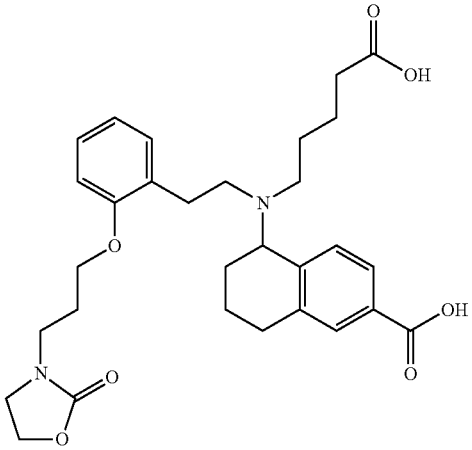<br>(racemate) | 20A[2)4)] | 72% or theory;<br>LC-MS (Method 2):<br>$R_t$ = 0.73 min,<br>m/z = 539 $[M + H]^+$ |

[1)] The ester hydrolysis was carried out using 5 N aqueous sodium hydroxide solution in THF/methanol (1 h under reflux);
[2)] The ester hydrolysis was carried out using 5 N aqueous sodium hydroxide solution in THF/methanol (overnight at RT);
[3)] The ester hydrolysis was carried out using 5 N aqueous sodium hydroxide solution in DMSO (overnight at RT);
[4)] Purification of the crude product was by preparative HPLC (Method 1).

General Procedure for the Preparation of Further Working Examples by Parallel Synthesis:

In each case 1.2 equivalents (0.12 mmol) of the alkyl halide in question were initially charged in a well of a 96-well deep well microtitre plate, and a solution of 47 mg (0.1 mmol) of the compound from Example 4A in 0.6 ml of DMF was added. 44 mg (0.32 mmol) of potassium carbonate were added to this mixture. The microtitre plate was covered and shaken at 80° C. overnight. The mixture was then filtered, 0.6 ml of 4 N aqueous sodium hydroxide solution was added to the filtrate and the mixture was covered again and shaken at 60° C. overnight. The solvent was then evaporated. The residue was taken up in 0.6 ml of DMSO and purified directly by preparative LC-MS (Method 8 or 9). The product-containing fractions were concentrated under reduced pressure using a centrifugal dryer. The residues of the individual fractions were in each case dissolved in 0.6 ml of DMSO and combined. The solvent was finally evaporated completely in a centrifugal drier.

The following compounds were obtained in accordance with this procedure:

| Example | Structure | LC-MS (Method 10) |
|---------|-----------|-------------------|
| 10 | 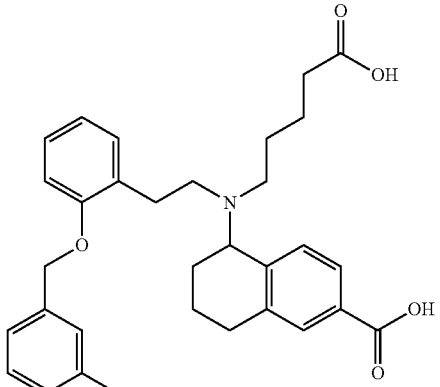<br>(racemate) | $R_t$ = 0.87 min,<br>m/z = 527 $[M + H]^+$ |

| Example | Structure | LC-MS (Method 10) |
|---|---|---|
| 11 | 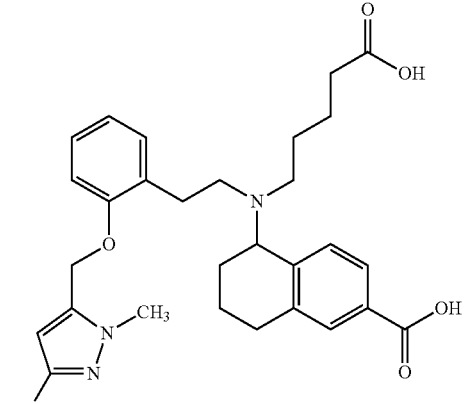<br>(racemate) | $R_t = 0.84$ min,<br>m/z = 520 $[M + H]^+$ |
| 12 | 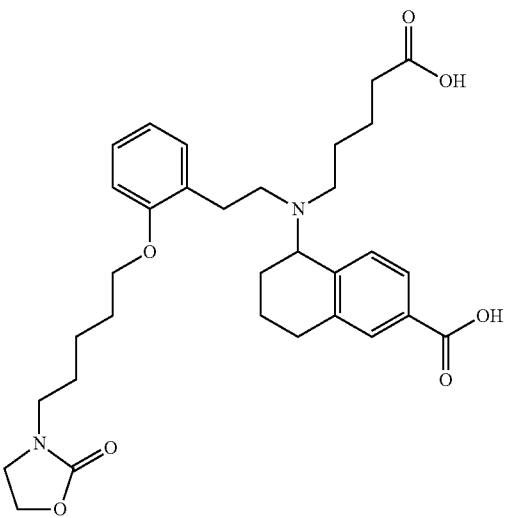<br>(racemate) | $R_t = 0.87$ min,<br>m/z = 567 $[M + H]^+$ |
| 13 | 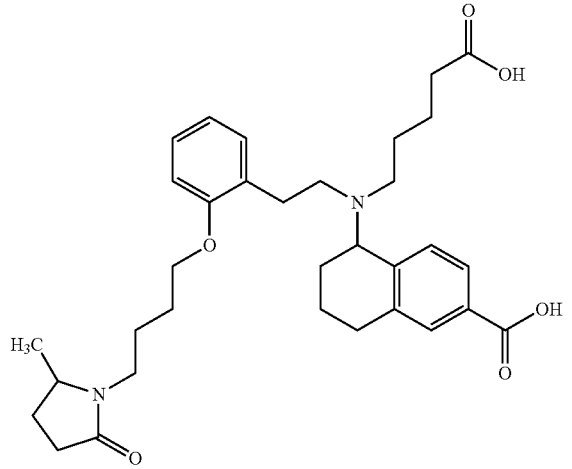<br>(racemate) | $R_t = 0.88$ min,<br>m/z = 565 $[M + H]^+$ |

-continued
| Example | Structure | LC-MS (Method 10) |
|---|---|---|
| 14 | 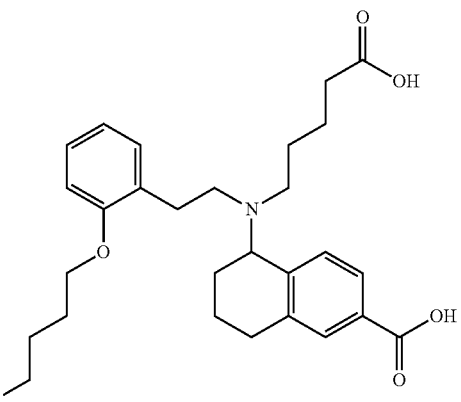 (racemate) | $R_t$ = 0.88 min, m/z = 565 [M + H]$^+$ |
| 15 | 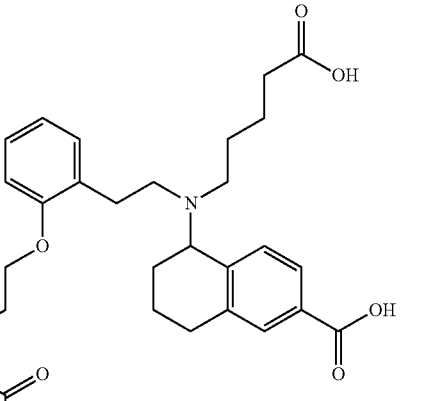 (racemate) | $R_t$ = 0.86 min, m/z = 551 [M + H]$^+$ |
| 16 | 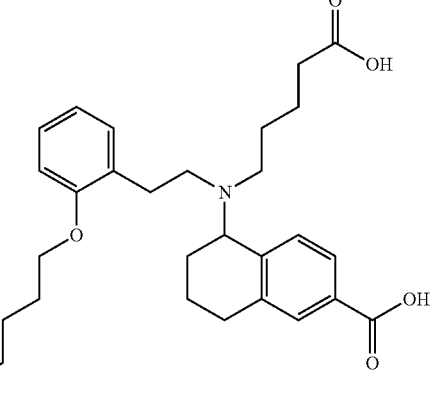 (racemate) | $R_t$ = 0.85 min, m/z = 551 [M + H]$^+$ |

B. Assessment of Pharmacological Efficacy

The pharmacological efficacy of the inventive compounds can be shown in the following assays:

B-1. Effect on a Recombinant Guanylate Cyclase Reporter Cell Line

The cellular activity of the compounds according to the invention is determined using a recombinant guanylate cyclase reporter cell line, as described in F. Wunder et al., *Anal. Biochem.* 339, 104-112 (2005).

Representative results for the compounds according to the invention are listed in Table 1:

TABLE 1 sGC-activating activity in the CHO reporter cell in vitro

| Example No. | MEC [nM] |
| --- | --- |
| 1 | 0.3 |
| 2 | 0.2 |
| 3 | 0.65 |
| 4 | 3.0 |
| 8 | 0.3 |
| 10 | 1000 |

(MEC = minimum effective concentration).

B-2. Stimulation of sGC Enzyme Activity

Soluble guanylate cyclase (sGC) converts on stimulation GTP into cGMP and pyrophosphate (PPi). PPi is detected with the aid of the assay described below. The signal produced in the assay increases as the reaction progresses and serves as a measure of the sGC enzyme activity under the given stimulation.

To carry out the assay, 29 µl of enzyme solution[0-10 nM soluble guanylate cyclase (prepared according to Honicka et al., *J. Mol. Med.* 77, 14-23 (1999)) in 50 mM TEA, 2 mM $MgCl_2$, 0.1% BSA (fraction V), 0.005% Brij®, pH 7.5] are initially introduced into a microplate, and 1 µl of the substance to be tested (as a serially diluted solution in DMSO) is added. The mixture is incubated at room temperature for 10 min. Then 20 µl of detection mix [1.2 nM Firefly Luciferase (*Photinus pyralis* luciferase, Promega), 29 µM dehydroluciferin (prepared according to Bitler & McElroy, *Arch. Biochem. Biophys.* 72, 358 (1957)), 122 µM luciferin (Promega), 153 µM ATP (Sigma) and 0.4 mM DTT (Sigma) in 50 mM TEA, 2 mM $MgCl_2$, 0.1% BSA (fraction V), 0.005% Brij®, pH 7.5] are added. The enzyme reaction is started by adding 20 µl of substrate solution[1.25 mM guanosine 5'-triphosphate (Sigma) in 50 mM TEA, 2 mM $MgCl_2$, 0.1% BSA (fraction V), 0.005% Brij®, pH 7.5] and measured continuously in a luminometer. The extent of the stimulation by the substance to be tested can be determined relative to the signal of the unstimulated reaction.

The activation of haem-free guanylate cyclase is examined by addition of 25 µM of 1H-1,2,4-oxadiazolo[4,3-a]quinoxalin-1-one (ODQ) to the enzyme solution and subsequent incubation for 30 minutes and compared to the stimulation of the native enzyme.

Representative results for the compounds according to the invention are listed in Table 2:

TABLE 2

Activating action at the sGC enzyme in vitro

| Example No. | MEC [nM] | $EC_{50}$ [nM] |
| --- | --- | --- |
| 1 | 0.34 | 3 |
| 2 | 0.11 | 2.5 |
| 3 | 5 | 43 |
| 4 | 0.21 | 4.5 |
| 8 | 0.32 | 7.2 |
| 10 | 270 | |
| 11 | 610 | |
| 13 | 55 | |
| 16 | 600 | |

(MEC = minimum effective concentration;
$EC_{50}$ = half-maximal effective concentration).

B-3. Vasorelaxant Effect In Vitro

Rabbits are anaesthetized by intravenous injection of thiopental sodium or killed (about 50 mg/kg) and exsanguinated. The arteria saphena is removed and divided into 3 mm wide rings. The rings are individually mounted on in each case one triangular pair of hooks, open at the end, made of 0.3 mm strong special wire (Remanium®). Under pretension, each ring is transferred into 5 ml organ baths containing carbogen-gassed Krebs-Henseleit solution of a temperature of 37° C. having the following composition: NaCl 119 mM; KCl 4.8 mM; $CaCl_2 \times 2\ H_2O$ 1 mM; $MgSO_4 \times 7\ H_2O$ 1.4 mM; $KH_2PO_4$ 1.2 mM; $NaHCO_3$ 25 mM; glucose 10 mM; bovine serum albumin 0.001%. The contractile force is determined with Statham UC2 cells, amplified and digitalized using A/D transducers (DAS-1802 HC, Keithley Instruments Munich), and recorded in parallel on linear recorders. Contractions are induced by addition of phenylephrin.

After several (in general 4) control cycles, the substance to be investigated is added in each further passage in increasing dosage, and the height of the contraction achieved under the influence of the test substance is compared with the height of the contraction achieved in the last preliminary passage. From this, the concentration which is necessary in order to reduce the contraction achieved in the preliminary control by 50% ($IC_{50}$) is calculated. The standard administration volume is 5 µl. The proportion of DMSO in the bath solution corresponds to 0.1%.

Representative results for the compounds according to the invention are listed in Table 3:

TABLE 3

Vasorelaxant effect in vitro

| Example No. | $IC_{50}$ [nM] |
| --- | --- |
| 1 | 6 |
| 2 | 3.8 |
| 3 | 58 |
| 4 | 31 |

B-4. Bronchodilating Effect In Vitro and In Vivo

B-4.1 Bronchorelaxation In Vitro

Bronchial rings (2-3 segments) are removed from rat, mouse or guinea pig and individually mounted in each case on a triangular pair of hooks, made from special wire of a diameter of 0.3 mm (Remanium®), which is open at the end. With pretension applied, each ring is introduced into 5 ml organ baths containing carbogen-gassed buffer solution of a temperature of 37° C. (for example Krebs-Henseleit solution). The bronchial rings are precontracted with methacholine (1 µM) to then examine bronchorelaxation by addition of increasing concentrations ($10^{-9}$ bis $10^{-6}$ M) of the respective test substance. The results are evaluated as percent relaxation with reference to the preconstriction by methacholine.

B-4.2 Animal Experiment Examining the Effect on Bronchoconstriction in the Asthma Model Prior to the provocation test, all animals (rats, mice) are treated intragastrally with a stomach tube or inhalatively. Here, the animals of the treatment groups receive the test substance, the control animals correspondingly receive a vehicle solution. After the waiting period, the animals are anaesthetized and intubated. Once an oesophagus catheter has been placed and a steady state of respiration has been reached, the lung function is initially measured prior to provocation. Measured parameters are, among others, lung resistance (RL) and dynamic compliance (Cdyn), and also tidal volume (TV) and respiratory frequency (f). Data storage and statistical evaluation are carried out using calculation programs specifically developed for these lung function tests (Notocord HEM).

This is followed by defined inhalative exposure of the test animals to a methacholine (MCh) aerosol (model of an unspecifically induced asthmatic bronchoconstriction). Recording of lung function parameters is continued during and 3 minutes after the exposure. MCh concentration and dose in the inhalation air are controlled and monitored using a developed feedback dose control system (via measuring aerosol concentration and minute volume). The test is stopped when the target dose is achieved. The inhibitory effect of the test substances is determined by the increase in resistance in comparison with the sham-treated positive control.

Study in the Allergic Asthma Model:

All animals except for the negative control are systemically sensitized with the allergen ovalbumin and adjuvans (alum). Instead, the negative control group receives physiological saline (NaCl). All groups are then provoked with ovalbumin. The study employs 6 treatment groups—2 test substances in 3 dose groups each; in addition, there is a reference group treated with dexamethasone i.p., a sham-treated and -challenged negative control group and a sham-treated and ovalbumin-provoked positive control group. Sensitization, treatment and challenge protocol: on day 0, 14 and 21, all animals are sensitized with ovalbumin and adjuvans i.p., the negative control is treated with NaCl. On day 28 and 29, the animals are provoked by intratracheal administration of ovalbumin solution. The test substances are administered intragastrally or inhalatively 1 h prior to each intratracheal allergen challenge. 18 h and 1 h prior to each intratracheal allergen provocation, a reference group is treated with dexamethasone i.p. The positive and the negative control group are treated correspondingly with the vehicle.

Airway Hyperreactivity and Inflammatory Response:

The animals are initially examined for airway hyperreactivity to unspecific stimuli. To this end, a hyperreactivity test in the form of a gradually increasing inhalative methacholine provocation is carried out about 24 h after ovalbumine challenge.

The animals are anaesthetized and orotracheally intubated, and prior to the provocation the lung function is measured body-plethysmographically (incl. parameters such as tidal volume, respiratory frequency, dynamic compliance and lung resistance). Once the measurements have been concluded, the dose/activity curve is plotted for each animal and the hyperreactivity of the positive control is evaluated with respect to the negative control or its inhibition in the treatment groups.

The animals are then sacrificed painlessly, blood samples are taken and the lungs are subjected to lavage (BAL). The lavage fluid is used to determine total cell number and differential blood count including the number of eosinophiles in the BAL. The remaining amounts of BAL fluid are initially frozen. This allows additional parameters (e.g. cytokines) to be determined at a later stage, if required. The lung tissue is stored for an optional histopathological examination.

B-5. Isolated Perfused Heart According to Langendorff

Male Wistar rats (strain HsdCpb:WU) of a body weight of 200-250 g are anaesthetized with Narcoren® (100 mg/kg). The thorax is opened and the heart is then exposed, excised and connected to a Langendorff apparatus by placing a cannula into the aorta. The heart is perfused retrogradely at 9 ml/min at constant flow with a Krebs-Henseleit buffer solution (gassed with 95% $O_2$ and 5% $CO_2$, pH 7.4, 35° C.; composition in mmol/l: NaCl 118; KCl 3; $NaHCO_3$ 22; $KH_2PO_4$ 1.2; $MgSO_4$ 1.2; $CaCl_2$ 1.8; Glucose 10; Na pyruvate 2). To measure the contractility of the heart, a balloon, made of thin plastic film, which is attached to a PE tube and filled with water is introduced via an opening in the left auricle of the heart into the left ventricle. The balloon is connected to a pressure transducer. The end-diastolic pressure is adjusted to 5-10 mmHg via the balloon volume. The perfusion pressure is detected with the aid of a second pressure transducer. The data are sent via a bridge amplifier to a computer and registered.

Following an equilibration time of 40 min, the test substance in question is added in a final concentration of $10^{-7}$ mol/l of the perfusion solution for 20 min, which, as symptom of coronary dilation, leads to a reduction of the perfusion pressure. The hearts are then perfused without test substance for a further 120 min (wash-out phase). To determine the reversibility of the lowering of the perfusion pressure (wash-out score), the value of the perfusion pressure after 60 min of the wash-out phase is based on the maximum reduction of perfusion pressure by the test substance and expressed in percent. The wash-out score obtained in this manner is taken as a measure for the residence time of the test substance at the site of action.

B-6. Haemodynamics in the Anaesthetized Piglet

Healthy Gottingen Minipigs® Ellegaard (Ellegaard, Denmark) of both sexes and having a weight of 2-6 kg are used. The animals are sedated by i.m. administration of about 25 mg/kg ketamine and about 10 mg/kg azaperone. Anaesthesia is initiated by i.v. administration of about 2 mg/kg ketamine and about 0.3 mg/kg midazolam. Maintenance of anaesthesia is by i.v. administration of about 7.5-30 mg/kg/h ketamine and about 1-4 mg/kg/h midazolam (rate of infusion 1-4 ml/kg/h) and about 150 µg/kg/h pancuronium bromide (for example Pancuronium-Actavis). After intubation, the animals are ventilated by the ventilator at a constant respiratory volume (10-12 ml/kg, 35 breaths/min; Avea®, Viasys Healthcare, USA, or Engstrom Carestation, GE Healthcare, Freiburg, Germany) such that an end-tidal $CO_2$ concentration of about 5% is achieved. Ventilation is performed with room air, enriched with about 40% oxygen (normoxia). For the measurement of the haemodynamic parameters such as pulmonary arterial pressure (PAP), blood pressure (BP) and heart rate (HR), catheters are inserted into the carotid artery to measure the blood pressure, and a Swan-Ganz® catheter is introduced in a flow-directed manner via the jugular vein into the pulmonary artery. The haemodynamic signals are recorded and evaluated by means of pressure transducers (Combitransducer, B. Braun, Melsungen, Germany)/amplifiers and Ponemah® as data aquisition software.

After the instruments have been placed into the animals, continuos infusion of a thromboxane $A_2$ analogue is initiated to increase the pulmonary arterial pressure. About 0.3-0.75 µg/kg/min of 9,11-didesoxy-9α,11α-epoxymethanoprostaglandine $F_{2\alpha}$ (U-44069; Sigma, cat. no. D0400, or Cayman Chemical Company, cat. no. 16440), dissolved in physiological saline, are infused to achieve an increase of the mean pulmonary arterial pressure to values of over 25 mmHg 30 minutes after the start of the infusion, a plateau is reached, and the experiment is started.

The test substances are administered as i.v. infusion or by inhalation. For the preparation of the solution for inhalation, the following procedure is adopted: for an animal having a weight of 4 kg, to prepare the stock solution (300 µg/kg), 1.2 mg of the test compound are weighed out and dissolved in a total volume of 3 ml (1% DMSO, 99% 0.2% strength citric acid solution, 1 N aqueous sodium hydroxide solution to adjust the pH to 8). The solution is then diluted to the concentration employed using 0.2% strength citric acid which had been adjusted to pH 8 beforehand with aqueous sodium hydroxide solution. In each test, 3 ml of the solution of test compound per 4 kg animal are nebulized in the inhalation arm of the respiratory circuit using the Aeroneb® Pro nebulizer system. The mean nebulization time is about 7 min from the start of the nebulization.

B-7. Inhalative Administration of sGC Activators in PAH Animal Models

The experiments are carried out on anaesthetized Gottingen minipigs, anaesthetized rats or conscious, telemetrically instrumented dogs. Acute pulmonary hypertension is induced for example by infusion of a thromboxane $A_2$ analogon, by acute hypoxia treatment or hypoxia treatment over a number of weeks and/or by administration of monocrotaline. The test substances are nebulized using the Nebutec® or Aeroneb® Pro nebulizer system, by means of powder and/or solution applicators for experimental intratracheal administration (Liquid MicroSprayer®, Dry Powder Insufflator™, MicroSprayer®, Penn-Century Inc., Wyndmoor, Pa., USA) or after solid nebulization inserted into the inspiration arm of the ventilation. The substances are employed as solids or solutions depending on the molecular structure. The haemodynamic signals are recorded and evaluated by means of pressure transducers (Combitransducer, B. Braun, Melsungen, Germany)/amplifiers and Ponemah® or CardioMems® as data aquisition software. After long-term experiments (for example monocrotaline rat), is it also possible to carry out a histological evaluation.

B-8. Radiotelemetric Measurement of Blood Pressure and Heart Rate of Conscious Rats A commercially available telemetry system from Data Sciences International DSI, USA, is employed for the measurements on conscious rats described below. The system consists of 3 main components: (1) implantable transmitters (Physiotel® telemetry transmitter), (2) receivers (Physiotel® receiver), which are linked via a multiplexer (DSI Data Exchange Matrix) to a (3) data acquisition computer. The telemetry system makes it possible to continuously record blood pressure, heart rate and body motion of conscious animals in their usual habitat.

The studies are conducted on adult female Wistar rats with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 µm.

Transmitter Implantation:

The telemetry transmitters used (TA11 PA-C40, DSI) are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal®, Sanofi, 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer. Post-operatively, an antibiotic (Oxytetracyclin® 10%, 60 mg/kg s.c., 0.06 ml/100 g body weight, Beta-Pharma GmbH, Germany) for infection prophylaxis and an analgesic (Rimadyl®, 4 mg/kg s.c., Pfizer, Germany) are administered.

Substances and Solutions:

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose. A solvent-treated group of animals is used as control.

Test Procedure:

The telemetry measuring system is configured for 24 animals. Each experiment is registered under an experiment number.

Each of the instrumented rats living in the system is assigned a separate receiving antenna (1010 Receiver, DSI). The implanted senders can be activated externally via an installed magnetic switch and are switched to transmission during the pre-run of the experiment. The signals emitted can be detected online by a data acquisition system (Dataquest™ A.R.T. for Windows, DSI) and processed accordingly. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP), (4) heart rate (HR) and (5) activity (ACT).

The acquisition of measurements is repeated under computer control at 5-minute intervals. The source data obtained as absolute values are corrected in the diagram with the currently measured barometric pressure (Ambient Pressure Reference Monitor, APR-1) and stored as individual data. Further technical details are given in the extensive documentation from the manufacturer company (DSI).

Unless indicated otherwise, the test substances are administered at 9:00 am on the day of the experiment. Following the administration, the parameters described above are measured over 24 hours.

Evaluation:

After the end of the experiment, the acquired individual data are sorted using the analysis software (Dataquest™ A.R.T. 4.1 Analysis). The blank value is taken at the time 2 hours before substance administration, and the selected data set therefore encompasses the period from 7:00 am on the day of the experiment to 9:00 am on the following day.

The data are smoothed over a predefinable period by determination of the average (15-minute average) and transferred as a text file to a data storage medium. The measured values presorted and compressed in this way are transferred to Excel templates and tabulated. For each day of the experiment, the data obtained are stored in a dedicated file bearing the number of the experiment. Results and test protocols are stored in files in paper form sorted by numbers.

Literature:

K. Witte, K. Hu, J. Swiatek, C. Müssig, G. Ertl and B. Lemmer, *Experimental heart failure in rats: effects on cardiovascular circadian rhythms and on myocardial β-adrenergic signaling*, Cardiovasc. Res. 47 (2): 350-358 (2000).

C. Working Examples for Pharmaceutical Compositions

The compounds according to the invention can be converted to pharmaceutical formulations as follows:

Tablet:

Composition:

100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of inventive compound, lactose and starch is granulated with a 5% solution (w/w) of the PVP in water. The granules are dried and then mixed with the magnesium stearate for 5 minutes. This mixture is compressed in a conventional tablet press (see above for format of the tablet). The guide value used for the pressing is a pressing force of 15 kN.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol; the compound according to the invention is added to the suspension. The water is added while stirring. The mixture is stirred for about 6 h before swelling of the Rhodigel is complete.

Solution for Oral Administration:

Composition:

500 mg of the compound according to the invention, 2.5 g of polysorbate and 97 g of polyethylene glycol 400. 20 g of oral solution correspond to a single dose of 100 mg of the compound according to the invention.

Production:

The compound according to the invention is suspended in the mixture of polyethylene glycol and polysorbate with stirring. The stirring operation is continued until dissolution of the compound according to the invention is complete.

i.v. Solution:

The compound according to the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:

1. A compound of the formula (I)

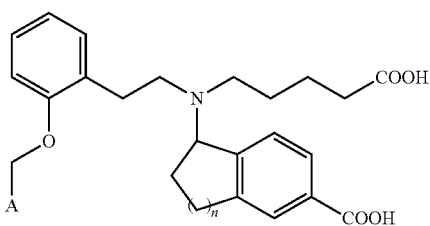

in which n represents the number 1 or 2 and

A represents a group of the formula

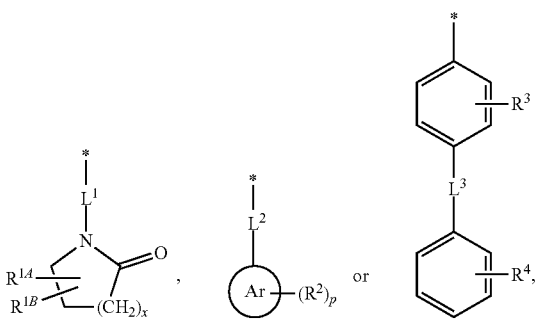

in which

* denotes the respective point of attachment to the remainder of the molecule, $L^1$ represents straight-chain $(C_1-C_5)$-alkanediyl, x represents the number 1, 2 or 3, where one of these $CH_2$ groups may be replaced by —O—, $R^{1A}$ and $R^{1B}$ independently of one another represent hydrogen or methyl, $L^2$ represents a bond or straight-chain $(C_1-C_5)$-alkanediyl, Ar represents phenyl or 5- or 6-membered heteroaryl having up to three heteroatoms from the group consisting of N, O and S, $R^2$ represents a substituent selected from the group consisting of fluorine, chlorine, bromine, cyano, $(C_1-C_4)$-alkyl, trifluoromethyl, $(C_1-C_4)$-alkoxy and trifluoromethoxy, p represents the number 0, 1 or 2, where in the case where the substituent $R^2$ occurs twice, its respective meanings can be identical or different, $L^3$ represents a bond, —O—, —$CH_2$—, —$CH_2$—$CH_2$— or —CH=CH— and $R^3$ and $R^4$ independently of one another represent hydrogen or a substituent selected from the group consisting of fluorine, chlorine, bromine, cyano, $(C_1-C_4)$-alkyl, trifluoromethyl, $(C_1-C_4)$-alkoxy and trifluoromethoxy, and salts, solvates and solvates of the salts thereof.

2. A compound of the formula (I) according to claim 1 in which
n represents the number 1 or 2
and
A represents a group of the formula

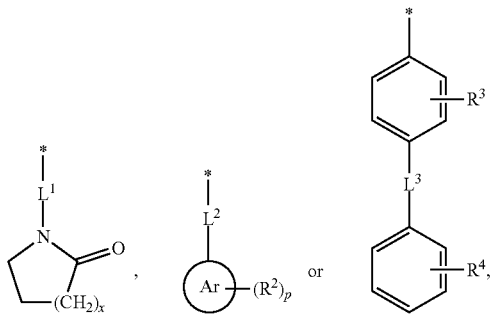

in which
* denotes the respective point of attachment to the remainder of the molecule,
$L^1$ represents straight-chain $(C_2\text{-}C_4)$-alkanediyl,
x represents the number 1 or 2, where one of these $CH_2$ groups may be replaced by —O—,
$L^2$ represents a bond or straight-chain $(C_1\text{-}C_4)$-alkanediyl,
Ar represents phenyl,
$R^2$ represents a substituent selected from the group consisting of fluorine, chlorine, cyano, $(C_1\text{-}C_4)$-alkyl and trifluoromethyl,
p represents the number 0 or 1,
$L^3$ represents a bond or —$CH_2$—$CH_2$—
and
$R^3$ and $R^4$ independently of one another represent hydrogen or a substituent selected from the group consisting of fluorine, chlorine, cyano, $(C_1\text{-}C_4)$-alkyl and trifluoromethyl,
and salts, solvates and solvates of the salts thereof.

3. A compound of the formula (I) according to claim 1 in which
n represents the number 1 or 2
and
A represents a group of the formula

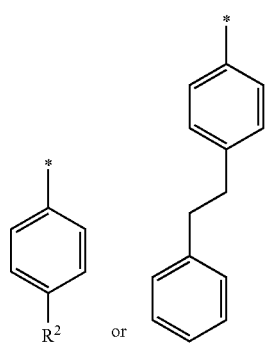

in which
* denotes the respective point of attachment to the remainder of the molecule
and
$R^2$ represents methyl, ethyl, isopropyl or tert-butyl,
and salts, solvates and solvates of the salts thereof.

4. A process for preparing the compound of the formula (I) as defined in claim 1, comprising reacting a compound of the formula (II)

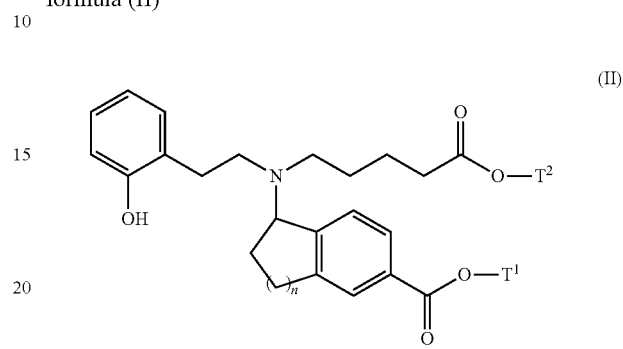

in which n has the meanings given in claim 1
and
$T^1$ and $T^2$ are identical or different and represent $(C_1\text{-}C_4)$-alkyl
in the presence of a base with a compound of the formula (III)

in which A has the meanings given in claim 1
and
$X^1$ represents a leaving group
to give a compound of the formula (IV)

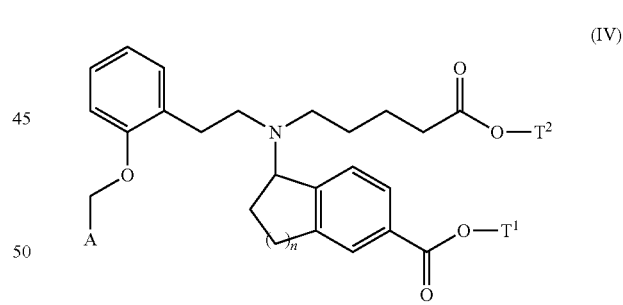

in which n, A, $T^1$ and $T^2$ each have the meanings given above,
converting the compound of the formula (IV) by hydrolysis of the ester groupings —C(O)$OT^1$ and —C(O)$OT^2$ into the corresponding dicarboxylic acid of the formula (I)
and optionally separating the resulting compounds of the formula (I) into the enantiomers and/or diastereomers thereof and/or optionally reacting the resulting compounds of the formula (I) with appropriate (i) solvents and/or (ii) bases or acids to give the solvates, salts and/or solvates of the salts thereof.

5. A medicament comprising the compound as defined in claim 1 in combination with one or more inert, nontoxic, pharmaceutically suitable excipients.

6. A medicament comprising the compound as defined in claim 1 in combination with one or more further active compounds selected from the group consisting of organic nitrates, NO donors, cGMP-PDE inhibitors, stimulators of guanylate cyclase, antithrombotic agents, hypotensive agents and lipid metabolism modifiers.

7. A method for treatment of heart failure, angina pectoris, hypertension, pulmonary hypertension, thromboembolic disorders, ischaemias, vascular disorders, impaired microcirculation, renal insufficiency, fibrotic disorders and arteriosclerosis in humans and animals by administration of an effective amount of at least one compound as defined in claim 1 to a human or animal in need thereof.

8. A method for the treatment of heart failure, angina pectoris, hypertension, pulmonary hypertension, thromboembolic disorders, ischaemias, impaired microcirculation, renal insufficiency, fibrotic disorders and arteriosclerosis in humans and animals by administration of an effective amount of the medicament of claim 5 to a human or animal in need thereof.

9. A method for the treatment of heart failure, angina pectoris, hypertension, pulmonary hypertension, thromboembolic disorders, ischaemias, impaired microcirculation, renal insufficiency, fibrotic disorders and arteriosclerosis in humans and animals by administration of an effective amount of the medicament of claim 6 to a human or animal in need thereof.

\* \* \* \* \*